(12) United States Patent
Lau et al.

(10) Patent No.: US 6,613,072 B2
(45) Date of Patent: *Sep. 2, 2003

(54) PROCEDURES FOR INTRODUCING STENTS AND STENT-GRAFTS

(75) Inventors: Lilip Lau, Sunnyvale, CA (US); Charles T. Maroney, Portola Valley, CA (US); William M. Hartigan, Fremont, CA (US); Sharon Lam, San Jose, CA (US)

(73) Assignee: Gore Enterprise Holdings, Inc., Newark, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/896,373

(22) Filed: Jul. 18, 1997

(65) Prior Publication Data

US 2002/0040236 A1 Apr. 4, 2002

Related U.S. Application Data

(63) Continuation of application No. 08/754,398, filed on Nov. 29, 1996, now abandoned, which is a continuation of application No. 08/361,793, filed on Dec. 21, 1994, now abandoned, which is a continuation-in-part of application No. 08/303,060, filed on Sep. 8, 1994, now abandoned.

(51) Int. Cl.[7] .................................................. A61F 2/06
(52) U.S. Cl. ........................ 623/1.11; 623/1.23; 623/1.2
(58) Field of Search .................................. 623/1, 11, 66, 623/1.15, 1.2, 1.23; 606/198, 108; 604/107, 109; 128/898

(56) References Cited

U.S. PATENT DOCUMENTS 2,638,093 A    5/1953   Kulick
3,029,819 A    4/1962   Starks
3,096,560 A    7/1963   Liebig (List continued on next page.)

FOREIGN PATENT DOCUMENTS

| AU | B-42485/89 | 4/1990 |
| AU | B-34742/93 | 8/1993 |
| CA | 2026604 | 4/1991 |

(List continued on next page.)

OTHER PUBLICATIONS

Blum, U. et al.; "Dacron Endografts for Infrarenal Abdominal Aortic Aneurysms: 2 Year Follow–Up"; Fifth international and Interdisciplinary Symposium on Endoluminal Stents and Grafts (Oct. 10–13, 1996) Washington, D.C., 2 pages total.

Chuter et al.; "Bifurcated stent–grafts for AAA: 3 year follow–up"; Abstracts from the Seventh International Course on Peripheral Vascular Intervention; J. Endovas. Surg. (1996) 3:453.

(List continued on next page.)

*Primary Examiner*—Paul B. Prebilic
(74) *Attorney, Agent, or Firm*—Morgan & Finnegan, LLP

(57) ABSTRACT

This invention is a medical device and a method of using it. The device is a foldable stent or stent-graft which may be percutaneously delivered with (or on) a catheter, typically an endovascular catheter, to a body cavity or lumen and then expanded. The stent's configuration allows it to be folded or otherwise compressed to a very small diameter prior to deployment without changing the length of the stent.

The deployment procedures may involve the use of an outer sleeve to maintain the stent or stent-graft at a reduced diameter or may involve one or more external or internal "slip-lines" or "tether wires" to hold and then to release the device. A removal slip line for holding the stent in the deployable configuration can be woven along longitudinal fold line using the sack knot.

14 Claims, 14 Drawing Sheets

U.S. PATENT DOCUMENTS

| | | |
|---|---|---|
| 3,142,067 A | 7/1964 | Liebig |
| 3,152,618 A | 10/1964 | Rothermel et al. |
| 3,174,851 A | 3/1965 | Buehur et al. |
| 3,351,463 A | 11/1967 | Rozner et al. |
| 3,479,670 A | 11/1969 | Medell |
| 3,514,791 A | 6/1970 | Sparks |
| 3,562,820 A | 2/1971 | Braun |
| 3,625,198 A | 12/1971 | Sparks |
| 3,657,744 A | 4/1972 | Ersek |
| 3,710,777 A | 1/1973 | Sparks |
| 3,753,700 A | 8/1973 | Harrison et al. |
| 3,774,596 A | 11/1973 | Cook |
| 3,805,301 A | 4/1974 | Liebig |
| 3,866,247 A | 2/1975 | Sparks |
| 3,866,609 A | 2/1975 | Sparks |
| 3,868,956 A | 3/1975 | Alfidi et al. |
| 3,927,422 A | 12/1975 | Sawyer |
| 3,938,524 A | 2/1976 | Sparks |
| 3,949,073 A | 4/1976 | Daniels et al. |
| 3,953,566 A | 4/1976 | Gore |
| 3,974,526 A | 8/1976 | Dardik et al. |
| 3,993,045 A | 11/1976 | Ion |
| 4,011,861 A | 3/1977 | Enger |
| 4,047,252 A | 9/1977 | Liebig |
| 4,130,904 A | 12/1978 | Whalen |
| 4,140,126 A | 2/1979 | Choudhury |
| 4,164,045 A | 8/1979 | Bokros et al. |
| 4,187,390 A | 2/1980 | Gore |
| 4,300,244 A | 11/1981 | Bokros |
| 4,306,318 A | 12/1981 | Mano |
| 4,319,363 A | 3/1982 | Ketharanathan |
| 4,355,426 A | 10/1982 | MacGregor |
| 4,411,655 A | 10/1983 | Schreck |
| 4,424,208 A | 1/1984 | Wallace et al. |
| 4,425,908 A | 1/1984 | Simon |
| 4,488,911 A | 12/1984 | Luck et al. |
| 4,494,531 A | 1/1985 | Gianturco |
| 4,502,159 A | 3/1985 | Woodroof |
| 4,503,569 A | 3/1985 | Dotter |
| 4,512,338 A | 4/1985 | Balko et al. |
| 4,517,687 A | 5/1985 | Liebig |
| 4,530,113 A | 7/1985 | Matterson |
| 4,546,500 A | 10/1985 | Bell |
| 4,553,545 A | 11/1985 | Maass et al. |
| 4,557,764 A | 12/1985 | Chu |
| 4,562,596 A | 1/1986 | Kornberg |
| 4,580,568 A | 4/1986 | Gianturco |
| 4,582,640 A | 4/1986 | Smestad et al. |
| 4,592,754 A | 6/1986 | Gupte |
| 4,604,762 A | 8/1986 | Robinson |
| 4,617,932 A | 10/1986 | Kornberg |
| 4,629,458 A | 12/1986 | Pinchuk |
| 4,641,653 A | 2/1987 | Rockey |
| 4,642,117 A | 2/1987 | Nguyen et al. |
| 4,647,416 A | 3/1987 | Seiler, Jr. et al. |
| 4,649,922 A | 3/1987 | Wiktor |
| 4,655,771 A | 4/1987 | Wallsten |
| 4,665,906 A | 5/1987 | Jervis |
| 4,689,399 A | 8/1987 | Chu |
| 4,728,328 A | 3/1988 | Hughes |
| 4,733,665 A | 3/1988 | Palmaz |
| 4,738,666 A | 4/1988 | Fuqua |
| 4,739,762 A | 4/1988 | Palmaz |
| 4,740,207 A | 4/1988 | Kreamer |
| 4,760,849 A | 8/1988 | Kropf |
| 4,776,337 A | 10/1988 | Palmaz |
| 4,787,899 A | 11/1988 | Lazarus |
| 4,790,313 A | 12/1988 | Borrelly |
| 4,795,458 A | 1/1989 | Regan |
| 4,798,606 A | 1/1989 | Pinchuk |
| 4,800,882 A | 1/1989 | Gianturco |
| 4,816,028 A | 3/1989 | Kapadia |
| 4,816,339 A | 3/1989 | Tu et al. |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,856,516 A | 8/1989 | Hillstead |
| 4,877,025 A | 10/1989 | Hanson |
| 4,878,906 A | 11/1989 | Lindemann et al. |
| 4,886,062 A | 12/1989 | Wiktor |
| 4,886,500 A | 12/1989 | Lazarus |
| 4,892,539 A | 1/1990 | Koch |
| 4,913,141 A | 4/1990 | Hillstead |
| 4,921,479 A | 5/1990 | Grayzel |
| 4,941,870 A | 7/1990 | Okada |
| 4,950,227 A | 8/1990 | Savin |
| 4,955,899 A | 9/1990 | Della Corna et al. |
| 4,957,504 A | 9/1990 | Cherdack |
| 4,957,508 A | 9/1990 | Kaneko et al. |
| 4,969,458 A | 11/1990 | Wiktor |
| 4,990,151 A | 2/1991 | Wallsten |
| 4,990,155 A | 2/1991 | Wilkoff |
| 4,994,071 A | 2/1991 | MacGregor |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,035,706 A | 7/1991 | Gianturco |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,042,161 A | 8/1991 | Hodge |
| 5,064,435 A | 11/1991 | Porter |
| 5,066,298 A | 11/1991 | Hess |
| 5,067,957 A | 11/1991 | Jervis |
| 5,078,726 A | 1/1992 | Kreamer |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,424 A | 4/1992 | Hoffman |
| 5,122,154 A | 6/1992 | Rhodes |
| 5,123,917 A | 6/1992 | Lee |
| 5,127,919 A | 7/1992 | Ibrahim |
| 5,133,732 A | 7/1992 | Wiktor |
| 5,139,480 A | 8/1992 | Hickle et al. |
| 5,147,370 A | 9/1992 | McNamara et al. |
| 5,151,105 A | 9/1992 | Kwan-Gett |
| 5,156,619 A | 10/1992 | Ehrenfeld |
| 5,161,547 A | 11/1992 | Tower |
| 5,162,430 A | 11/1992 | Rhee et al. |
| 5,163,958 A | 11/1992 | Pinchuk |
| 5,171,262 A | 12/1992 | MacGregor |
| 5,178,630 A | 1/1993 | Schmitt |
| 5,192,289 A | 3/1993 | Jessen |
| 5,192,307 A | 3/1993 | Wall |
| 5,195,984 A | 3/1993 | Schatz |
| 5,197,977 A | 3/1993 | Hoffman |
| 5,197,978 A | 3/1993 | Hess |
| 5,201,757 A | 4/1993 | Heyn |
| 5,209,735 A | 5/1993 | Lazarus |
| 5,211,658 A | 5/1993 | Clouse |
| 5,213,580 A | 5/1993 | Slepian et al. |
| 5,217,483 A | 6/1993 | Tower |
| 5,221,261 A | 6/1993 | Termin et al. |
| 5,226,913 A | 7/1993 | Pinchuk |
| 5,232,446 A | 8/1993 | Arney |
| 5,236,447 A | 8/1993 | Kubo et al. |
| 5,242,451 A | 9/1993 | Harada et al. |
| 5,246,452 A | 9/1993 | Sinnott |

| | | | | | | |
|---|---|---|---|---|---|---|
| 5,258,042 A | 11/1993 | Mehta | | 5,549,663 A | 8/1996 | Cottone, Jr. |
| 5,264,276 A | 11/1993 | McGregor et al. | | 5,552,961 A | 9/1996 | Vangall |
| 5,271,410 A | 12/1993 | Wolzinger | | 5,554,180 A | 9/1996 | Turk |
| 5,276,276 A | 1/1994 | Gunn | | 5,554,181 A | 9/1996 | Das |
| 5,282,824 A | 2/1994 | Gianturco | | 5,554,182 A | 9/1996 | Dinh |
| 5,282,846 A | 2/1994 | Schmitt | | 5,556,413 A | 9/1996 | Lam |
| 5,282,847 A | 2/1994 | Trescony et al. | | 5,562,724 A | 10/1996 | Vorwerk |
| 5,282,848 A | 2/1994 | Schmitt | | 5,562,726 A | 10/1996 | Chuter |
| 5,290,305 A | 3/1994 | Inoue | | 5,562,727 A | 10/1996 | Turk |
| 5,306,261 A | 4/1994 | Alliger et al. | | 5,571,166 A | 11/1996 | Dinh |
| 5,306,294 A | 4/1994 | Winston et al. | | 5,571,169 A | 11/1996 | Plaia |
| 5,314,472 A | 5/1994 | Fontaine | | 5,571,172 A | 11/1996 | Chin |
| 5,324,304 A | 6/1994 | Rasmussen | | 5,571,173 A | 11/1996 | Parodi |
| 5,324,323 A | 6/1994 | Bui | | 5,571,176 A | 11/1996 | Taheri |
| 5,330,528 A | 7/1994 | Lazim | | 5,575,815 A | 11/1996 | Slepian |
| 5,336,254 A | 8/1994 | Brennen | | 5,575,816 A | 11/1996 | Rudnick et al. |
| 5,342,348 A | 8/1994 | Kaplan | | 5,575,817 A | 11/1996 | Martin |
| 5,342,387 A | 8/1994 | Summers | | 5,578,071 A | 11/1996 | Parodi |
| 5,344,426 A | 9/1994 | Lau et al. | | 5,591,197 A * | 1/1997 | Orth et al. ............. 606/198 |
| 5,348,537 A | 9/1994 | Wiesner | | 5,591,198 A | 1/1997 | Boyle et al. |
| 5,354,308 A | 10/1994 | Simon et al. | | 5,591,228 A | 1/1997 | Edoga |
| 5,354,309 A | 10/1994 | Schnepp-Pesch et al. | | 5,591,229 A | 1/1997 | Parodi |
| 5,356,423 A | 10/1994 | Tihon et al. | | 5,599,305 A | 2/1997 | Hermann |
| 5,360,443 A | 11/1994 | Barone et al. | | 5,607,442 A | 3/1997 | Fischell et al. |
| 5,366,472 A | 11/1994 | Hillstead | | 5,607,444 A | 3/1997 | Lam |
| 5,366,473 A | 11/1994 | Winston et al. | | 5,607,445 A | 3/1997 | Summers |
| 5,366,504 A | 11/1994 | Andersen | | 5,609,625 A | 3/1997 | Piplani |
| 5,370,691 A | 12/1994 | Samson | | 5,609,627 A | 3/1997 | Goicoechea |
| 5,372,600 A | 12/1994 | Beyar | | 5,620,763 A | 4/1997 | House |
| 5,382,261 A | 1/1995 | Palmaz | | 5,622,188 A | 4/1997 | Plaia |
| 5,383,928 A | 1/1995 | Scott et al. | | 5,626,561 A | 5/1997 | Butler |
| 5,385,580 A | 1/1995 | Schmitt | | 5,628,783 A | 5/1997 | Quiachon |
| 5,387,235 A | 2/1995 | Chuter | | 5,628,784 A | 5/1997 | Strecker |
| 5,405,377 A * | 4/1995 | Cragg ............. 606/198 | | 5,628,788 A | 5/1997 | Pinchuk |
| 5,405,378 A | 4/1995 | Strecker | | 5,632,763 A | 5/1997 | Glastra |
| 5,413,598 A | 5/1995 | Moreland | | 5,632,772 A | 5/1997 | Alcime |
| 5,421,955 A * | 6/1995 | Lau et al. ............. 606/198 | | 5,637,113 A | 6/1997 | Tartaglia |
| 5,423,849 A * | 6/1995 | Engelson et al. ......... 606/198 | | 5,639,278 A | 6/1997 | Dereume |
| 5,425,710 A | 6/1995 | Khair et al. | | 5,643,208 A | 7/1997 | Parodi |
| 5,425,739 A | 6/1995 | Jessen | | 5,647,380 A | 7/1997 | Campbell |
| 5,443,500 A | 8/1995 | Sigwart | | 5,649,978 A | 7/1997 | Samson |
| 5,449,373 A | 9/1995 | Pinchasik et al. | | 5,653,743 A | 8/1997 | Martin |
| 5,453,084 A | 9/1995 | Moses | | 5,653,748 A | 8/1997 | Strecker |
| 5,456,713 A | 10/1995 | Chuter | | 5,662,614 A | 9/1997 | Edoga |
| 5,456,721 A | 10/1995 | LeGrand | | 5,662,675 A | 9/1997 | Polanskyj Stockert |
| 5,458,605 A | 10/1995 | Klemm | | 5,662,701 A | 9/1997 | Plaia |
| 5,458,615 A | 10/1995 | Klemm et al. | | 5,662,713 A | 9/1997 | Andersen et al. |
| 5,464,449 A | 11/1995 | Ryan | | 5,665,117 A | 9/1997 | Rhodes |
| 5,476,506 A | 12/1995 | Lunn | | 5,667,523 A | 9/1997 | Bynon |
| 5,480,423 A | 1/1996 | Ravenscroft et al. | | 5,669,924 A | 9/1997 | Shaknovich |
| 5,484,444 A | 1/1996 | Braudschweiler | | 5,669,930 A | 9/1997 | Igarashi |
| 5,487,858 A | 1/1996 | Schmitt | | 5,674,276 A | 10/1997 | Andersen |
| 5,489,295 A | 2/1996 | Piplani | | 5,676,671 A * | 10/1997 | Inoue ............. 606/108 |
| 5,496,364 A | 3/1996 | Schmitt | | 5,676,696 A | 10/1997 | Marcade |
| 5,496,365 A | 3/1996 | Sgro | | 5,676,697 A | 10/1997 | McDonald |
| 5,499,994 A | 3/1996 | Tihon | | 5,681,346 A | 10/1997 | Orth |
| 5,507,767 A | 4/1996 | Maeda et al. | | 5,683,449 A | 11/1997 | Marcadi |
| 5,507,769 A | 4/1996 | Marin | | 5,683,450 A | 11/1997 | Goicoechea |
| 5,507,771 A | 4/1996 | Gianturco | | 5,683,451 A | 11/1997 | Lenker |
| 5,509,902 A | 4/1996 | Raulerson | | 5,683,452 A | 11/1997 | Barone |
| 5,509,931 A | 4/1996 | Schmitt | | 5,693,084 A | 12/1997 | Chuter |
| 5,514,154 A | 5/1996 | Lau et al. | | 5,693,086 A | 12/1997 | Goicoechea |
| 5,522,822 A | 6/1996 | Phelps | | 5,693,087 A | 12/1997 | Parodi |
| 5,522,880 A | 6/1996 | Barone | | 5,693,088 A | 12/1997 | Lazarus |
| 5,522,881 A | 6/1996 | Lentz | | 5,695,517 A | 12/1997 | Marin |
| 5,522,961 A | 6/1996 | Leonhardt | | 5,697,970 A | 12/1997 | Schmitt |
| 5,540,701 A | 7/1996 | Sharkey et al. | | 5,700,285 A | 12/1997 | Myers |
| 5,540,712 A | 7/1996 | Kleshinski et al. | | 5,700,286 A | 12/1997 | Tartaglia et al. |
| 5,545,210 A | 8/1996 | Hess et al. | | 5,709,657 A | 1/1998 | Zimmon |
| 5,545,211 A | 8/1996 | An | | 5,713,917 A | 2/1998 | Leonhardt |
| 5,549,635 A | 8/1996 | Solar | | 5,716,365 A | 2/1998 | Goicoechea |

| | | |
|---|---|---|
| 5,718,724 A | 2/1998 | Goicoechea |
| 5,718,973 A | 2/1998 | Lewis |
| 5,720,776 A | 2/1998 | Chuter |
| 5,723,003 A | 3/1998 | Winston |
| 5,723,004 A | 3/1998 | Dereume |
| 5,728,131 A | 3/1998 | Frantzen |
| 5,728,150 A | 3/1998 | McDonald |
| 5,730,698 A | 3/1998 | Fischell |
| 5,732,572 A | 3/1998 | Litton |
| 5,735,892 A * | 4/1998 | Myers et al. ............... 623/1 |
| 5,741,274 A | 4/1998 | Lenker |
| 5,741,325 A | 4/1998 | Chaikof |
| 5,749,825 A | 5/1998 | Fischell |
| 5,749,880 A | 5/1998 | Banas |
| 5,749,921 A | 5/1998 | Lenker et al. |
| 5,755,769 A | 5/1998 | Richard et al. |
| 5,769,882 A | 6/1998 | Fogarty |
| 5,779,732 A | 7/1998 | Amundson |
| 5,782,904 A | 7/1998 | White |
| 5,800,521 A | 9/1998 | Orth |
| 5,800,522 A | 9/1998 | Campbell |
| 5,800,524 A | 9/1998 | Borghi |
| 5,810,870 A | 9/1998 | Myers |
| 5,824,041 A | 10/1998 | Lenker |
| 5,843,069 A | 12/1998 | Butler |
| 5,843,171 A | 12/1998 | Campbell |
| 5,865,723 A | 2/1999 | Love |
| 5,868,704 A | 2/1999 | Campbell |
| 5,873,906 A * | 2/1999 | Lau et al. ............... 623/66 |
| 5,876,432 A | 3/1999 | Lau |
| 5,888,243 A | 3/1999 | Silverstrini |
| 5,919,225 A | 7/1999 | Lau |
| 5,925,061 A | 7/1999 | Oggi |
| 5,925,075 A | 7/1999 | Myers |
| 5,961,546 A | 10/1999 | Robinson |
| 5,972,441 A | 10/1999 | Campbell |
| 5,976,650 A | 11/1999 | Campbell |
| 5,993,489 A | 11/1999 | Lewis |
| 6,001,123 A | 12/1999 | Lau |
| 6,015,429 A | 1/2000 | Lau |
| 6,015,431 A | 1/2000 | Thornton |
| 6,017,362 A | 1/2000 | Lau |
| 6,019,787 A | 2/2000 | Richard |
| 6,019,788 A | 2/2000 | Butters |
| 6,025,044 A | 2/2000 | Campbell |
| 6,027,779 A | 2/2000 | Campbell |
| 6,027,811 A | 2/2000 | Campbell |
| 6,042,605 A | 3/2000 | Martin |
| 6,048,484 A | 4/2000 | House |
| 6,086,604 A * | 7/2000 | Fischell et al. ............ 606/198 |
| 6,120,477 A | 9/2000 | Campbell |
| 6,139,572 A | 10/2000 | Campbell |
| 6,159,565 A | 12/2000 | Campbell |
| 6,165,210 A | 12/2000 | Lau |
| 6,193,745 B1 | 2/2001 | Fogarty |
| 6,203,568 B1 | 3/2001 | Lombardi et al. |

FOREIGN PATENT DOCUMENTS

| | | |
|---|---|---|
| CA | 2079417 | 4/1993 |
| DE | 37 24 514 A1 | 2/1989 |
| DE | 39 18 736 A1 | 12/1990 |
| DE | 41 37 857 A1 | 5/1992 |
| DE | 196 17 823 A | 11/1997 |
| EP | 0382014 | 8/1990 |
| EP | 0408245 | 1/1991 |
| EP | 0 408 245 A1 | 1/1991 |
| EP | 0 418 677 | 3/1991 |
| EP | 0 423 916 B1 | 4/1991 |
| EP | 0 435 518 A1 | 7/1991 |
| EP | 0 464 755 A1 | 1/1992 |
| EP | 0472731 * | 3/1992 |
| EP | 0540290 | 5/1993 |
| EP | 0 551 179 A1 | 7/1993 |
| EP | 0556850 | 8/1993 |
| EP | 0565251 | 10/1993 |
| EP | 0 667 131 A2 | 1/1995 |
| EP | 0686379 | 12/1995 |
| EP | 0 689 806 A2 | 1/1996 |
| EP | 0 696 447 A2 | 2/1996 |
| EP | 0 701 800 A1 | 3/1996 |
| EP | 0 705 577 A1 | 4/1996 |
| EP | 0 716 834 A1 | 6/1996 |
| EP | 0 747 020 A2 | 12/1996 |
| FR | 2 678 508 | 1/1993 |
| GB | 1 506 432 | 4/1978 |
| GB | 1 567 122 | 5/1980 |
| GB | 1 355 373 | 6/1994 |
| JP | 02-174859 | 7/1990 |
| JP | 06-007454 | 1/1994 |
| JP | 06-181993 | 7/1994 |
| JP | 07-500272 | 1/1995 |
| JP | 07-024688 | 3/1995 |
| JP | 8-509899 | 10/1996 |
| SU | 1635980 A1 | 12/1988 |
| WO | WO 88/06026 | 8/1988 |
| WO | WO 90/04982 | 5/1990 |
| WO | WO 92/03107 | 3/1992 |
| WO | WO 92/04097 | 3/1992 |
| WO | WO 92/06734 | 4/1992 |
| WO | WO 92/09246 | 6/1992 |
| WO | WO 93/13825 | 7/1993 |
| WO | WO 93/17636 | 9/1993 |
| WO | WO 93/19803 | 10/1993 |
| WO | WO 93/19804 | 10/1993 |
| WO | WO 93/22984 | 11/1993 |
| WO | WO 93/22986 | 11/1993 |
| WO | WO 93/22989 | 11/1993 |
| WO | WO 94/00179 | 1/1994 |
| WO | WO 94/01483 | 1/1994 |
| WO | WO 94/04097 | 3/1994 |
| WO | WO 94/12136 | 6/1994 |
| WO | WO 94/15549 | 7/1994 |
| WO | WO 95/01466 | 1/1995 |
| WO | WO 95/05131 | 2/1995 |
| WO | WO 95/05132 | 2/1995 |
| WO | WO 95/09586 | 4/1995 |
| WO | WO 95/21592 | 8/1995 |
| WO | WO 95/26695 | 10/1995 |
| WO | WO 96/10967 | 4/1996 |
| WO | WO 96/18360 | 6/1996 |
| WO | WO 96/18361 | 6/1996 |
| WO | WO 96/24306 | 8/1996 |
| WO | WO 97/21402 | 6/1997 |
| WO | WO 97/21403 | 6/1997 |
| WO | WO 97/21641 | 6/1997 |
| WO | WO 98/30173 | 7/1998 |

OTHER PUBLICATIONS

Chuter et al.; "Bifurcated stent–grafts for AAA: 3 year follow–up"; Fifth International and Interdisciplinary Symposium on Endoluminal Stents and Grafts (Oct. 10–13, 1996) Washington, D.C., 2 pages total.

Cragg, et al.; "Percutaneous Femoropopliteal Graft Placement" Journal of Vascular and Interventional Radiology 4(4): 455–462 (1993).

Dereume, JP et al.; "Endoluminal Treatment Of Abdominal Aortic Aneurysm with the Corvita Endovascular Graft, Results of a Single–Center, Prospective Feasibility Study of 90 Patients"; Abstracts from the Seventh International Course on Peripheral Vascular Intervention J. Endovasc. Surg. (1996) 3:460–461.

Hagen et al., "Self–Expandable Macroporous Nitinol Stents for Transfemoral Exclusion of Aortic Aneurysm in Dogs" Cardiovascular Intervention Radiology 16:339–342 (1993).

Katzen et al., "Initial experience performing combined surgical/interventional procedures in the interventional suite" Abstracts from the Seventh International Course on Peripheral Vascular Intervention J. Endovasc. Surg. (1996) 3:467.

Moore et al., "Transfemoral endovascular repair of abdominal aortic aneurysm: Result of the North American EVT phase 1 trial" J. Vasc. Surg. (1996) 23:543–552.

Parodi et al., "long–term follow–up AAA endoluminal repair" Abstracts from the Seventh International Course on Peripheral Vascular Intervention. J. Endovasc. Surg. (1996) 3:335.

Product Brochure for Cook–ZTM Stents, Gianturco–Rosch Biliary Design, CookR, A Cook Groups Company, P.O. Box 489, Bloomington, IN, 47402, U.S.A., 4 pages total, (1989).

Product Brochure for PalmazTM Balloon–Expandable Stent, Johnson & Johnson Interventional Systems, 40 Technology Drive, P.O. Box 4917, Warren, NJ, 07059, 2 pages total, (1990).

White et al., "Endoleak following endoluminal repair of AAA: Diagnosis, significance, and amanagement" Abstracts from the Seventh International Course on Peripheral Vascular Intervention J. Endovasc. Surg. (1996) 3:339–340.

Wilson et al.; "A self expanding bifurcated endovascular graft for Abdominal Aortic Aneurysm Repair. An Initial Study in a Canine Model" ASAIO Journal 42(5): 386–393 (1996).

World Medical News, World Medical manufacturing Corporation, 13794 NW 4th Street, Bldgs. 210 & 211, Sunrise, Florida, 33325 U.S.A., vol. 5, Issue 3 (Jul. 1996) 3 pages total.

U.S. patent application Ser. No. 08/903,210, Lau et al., filed Jul. 21, 1997, pending.

U.S. patent application Ser. No. 08/871,427, Lau et al., filed Jun. 9, 1997, pending.

U.S. patent application Ser. No. 09/376,931, Martin et al., filed Aug. 13, 1999, pending.

U.S. patent application Ser. No. 08/896,804, Van der Burg et al., filed Jul. 18, 1997, pending.

U.S. patent application Ser. No. 08/772,373, Leopold et al., Dec. 23, 1996, pending.

U.S. patent application Ser. No. 08/772,372, Thorton et al, filed Dec. 23, 1996, pending.

Cragg et al.; *Nitinol Intravascular Stent: Results of Preclinical Evaluation; Radiology*; pp 775–778; Dec. 1993; vol. 189, No. 3.

Laborde et al., "Intraluminal Bypass of Abdominal Aortic Aneurysm: Feasibility Study"; *Radiology* 1992, 184:185–190.

MinTec™ Minimally Invasive Technologies Product Brochure for the Craggstent and Cragg EndoPro System 1, 4 pages total.

Cragg, "Percutaneous femoropopliteal graft placement" *Radiology* (1993) 4(4):455–462.

Product Brochure for Catheters, Guidewires, and Stents Schneider (USA) Inc., Pfizer Hospital Products Group, 5905 Nathan Lane, Minneapolis, Minnesota, 55442 (1995).

U.S. patent application Ser. No. 09/207,944, Vonesh et al., filed Dec. 9, 1998.

U.S. patent application Ser. No. 09/235,214, Brauker et al., filed Jan. 22, 1999.

U.S. patent application Ser. No. 09/235,458, Vonesh et al., filed Jan. 22, 1999.

U.S. patent application Ser. No. 09/306,522, Myers, filed May 6, 1999.

U.S. patent application Ser. No. 09/408,866, Brenton et al., filed Sep. 30, 1999.

U.S. patent application Ser. No. 09/488,229, Cully et al., filed Jan. 20, 2000.

U.S. patent application Ser. No. 09/489,604, Vonesh et al., filed Jan. 20, 2000.

U.S. patent application Ser. No. 09/510,937, Goffena et al., filed Feb. 22, 2000.

* cited by examiner

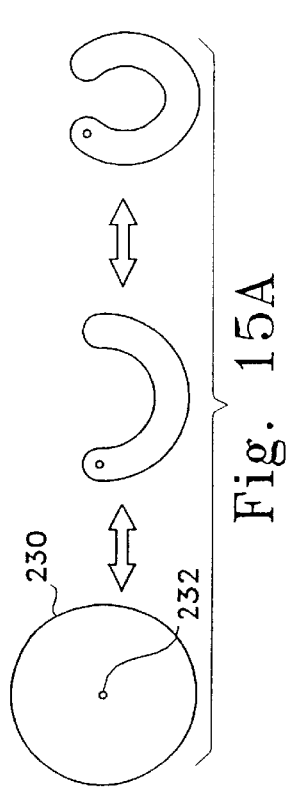
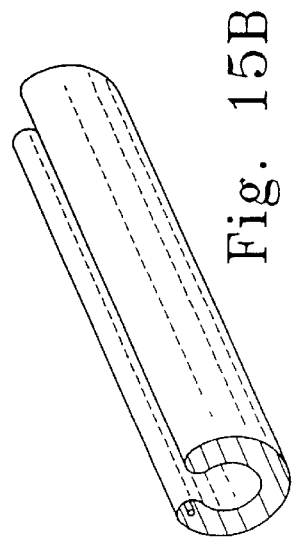
Fig. 15A                    Fig. 15B
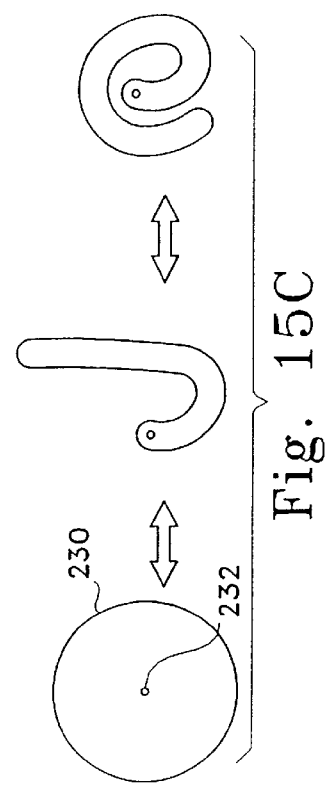
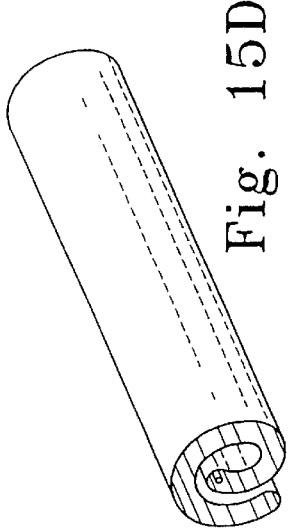
Fig. 15C                    Fig. 15D
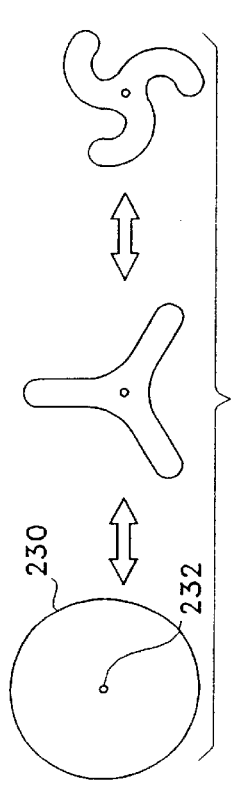
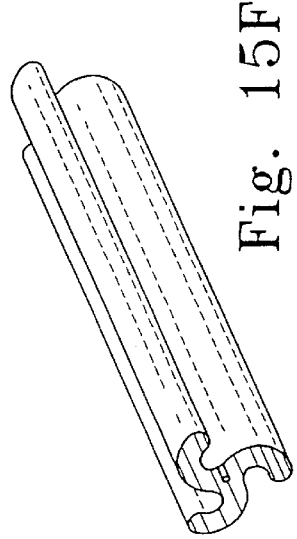
Fig. 15E                    Fig. 15F

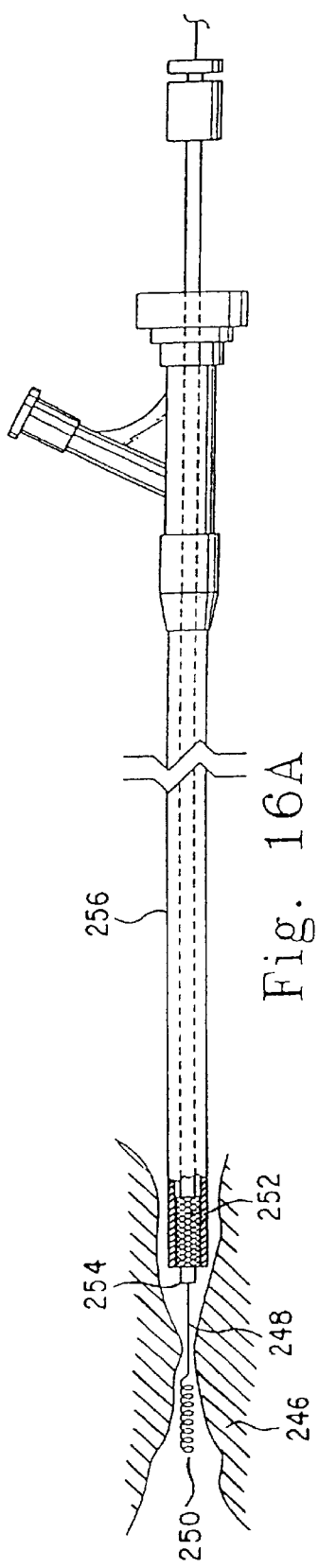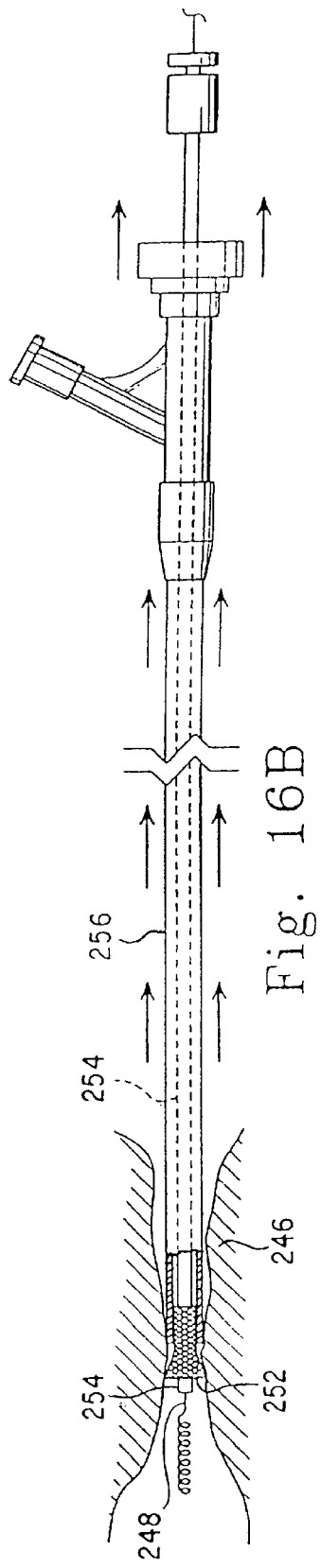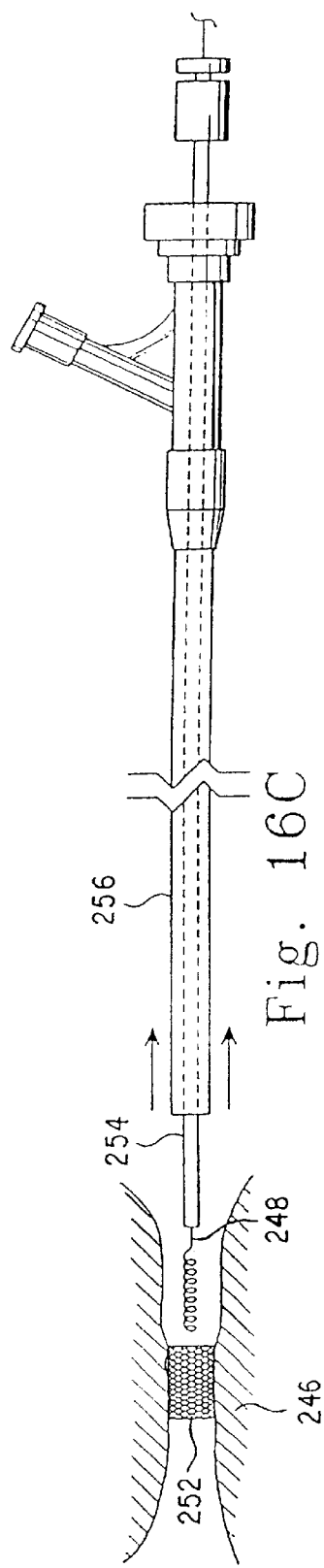

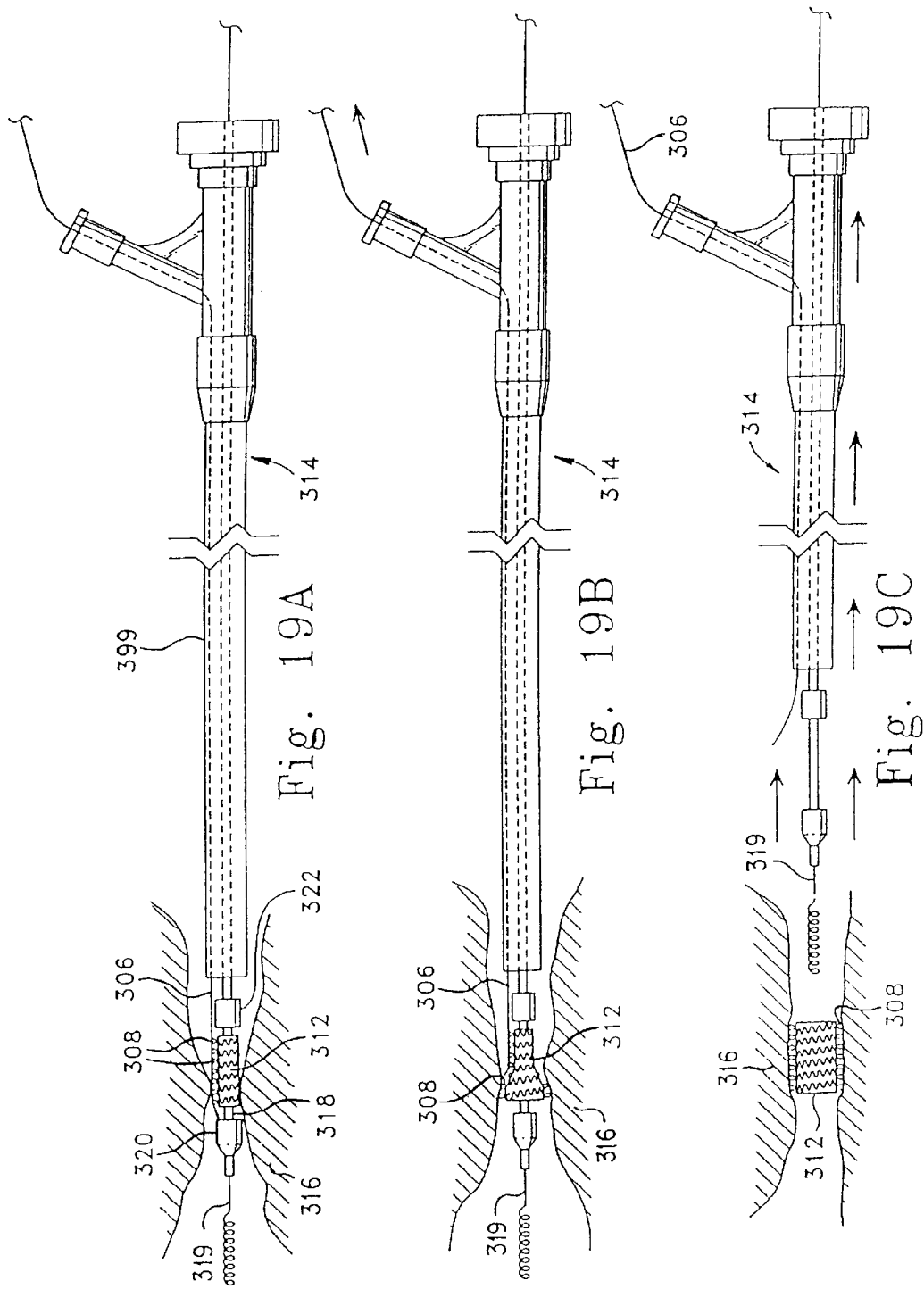

PROCEDURES FOR INTRODUCING STENTS AND STENT-GRAFTS

This is a Continuation of U.S. patent application Ser. No. 08/754,398 filed Nov. 29, 1996, which is a Continuation of U.S. patent application Ser. No. 08/361,793 filed Dec. 21, 1994, which is a continuation-in-part of U.S. patent application Ser. No. 08/303,060 filed Sep. 8, 1994, each of which is now abandoned.

FIELD OF THE INVENTION

This invention is a medical device and a method of using it. The device is a foldable stent or stent-graft which may be percutaneously delivered with (or on) a catheter, typically an endovascular catheter, to a body cavity or lumen and then expanded. It may also be delivered via surgical (or other) techniques. The expandable stent structure utilizes torsional members which distribute bending and folding loads in such a way that the stent is not plastically deformed. The stent's configuration allows it to be folded or otherwise compressed to a very small diameter prior to deployment without changing the length of the stent. The graft component cooperating with the stent is tubular and preferably is blood-compatible material which may, if desired, be reinforced with fibers. The stent is able to provide collapsible support for otherwise frangible graft material.

The invention also involves procedures for folding stents and for deploying stents or stent-grafts which have been folded, bound, or otherwise collapsed to significantly smaller diameters for insertion into a human or animal body. When used with super-elastic alloys, the stent may be collapsed at a convenient temperature either above or, preferably, below the transition temperature of the alloy. The deployment procedures may involve the use of an outer sleeve to maintain the stent or stent-graft at a reduced diameter or may involve one or more external or internal "slip-lines" or "tether wires" to hold and then to release the device.

BACKGROUND OF THE INVENTION

Treatment or isolation of vascular aneurysms or of vessel walls which have been thinned or thickened by disease has traditionally been done via surgical bypassing with vascular grafts. Shortcomings of this procedure include the morbidity and mortality associated with surgery, long recovery times after surgery, and the high incidence of repeat intervention needed due to limitations of the graft or of the procedure. Vessels thickened by disease are currently sometimes treated less invasively with intraluminal stents that mechanically hold these vessels open either subsequent to or as an adjunct to a balloon angioplasty procedure. Shortcomings of current stents include the use of highly thrombogenic materials (stainless steels, tantalum, ELGILOY) which are exposed to blood, the general failure of these materials to attract and support functional endothelium, the irregular stent/vessel surface that causes unnatural blood flow patterns, and the mismatch of compliance and flexibility between the vessel and the stent.

Important to this invention is the use of less invasive intraluminal delivery and, desirably, placement of a non-thrombogenic blood-carrying conduit having a smooth inner lumen which will endothelize. One desirable biologic material for the inner layer of the inventive stent-graft is collagen-based and, although it will fold with ease, is otherwise fairly frangible or inelastic in that it has very little ability to stretch. Mounting a collagen tube on the outside of or as a part of a balloon-expandable stent will usually cause the tube to tear. Mounting such a tube on the inside of a balloon expandable stent will yield a torn irregular surface exposed to blood flow. Further, balloon expandable devices that rely upon plastic deformation of the stent to achieve a deployed shape are subject to abrupt closure as a result of trauma when the devices are placed in a vessel near the skin surface or across a joint or ligament. Those self-expanding stents which rely on the shortening of the stent upon radial expansion at deployment may cause vessel tearing problems similar to those observed with the use of balloon expandable devices. Obviously, stents which shorten during deployment are also subject to deployment placement inaccuracies.

The most desired variations of this invention involve a stent-graft which is self-expanding, which does not shorten upon delivery, which has excellent longitudinal flexibility, which has high radial compliance to the vessel lumen, and exposes the blood to a smooth, nonthrombogenic surface often capable of supporting endothelium growth.

The inventive device may be delivered in a reduced diameter and expanded to maintain the patency of any conduit or lumen in the body. An area in which the inventive stent and stent graft is particularly beneficial is in the scaffolding of atherosclerotic lesions in the cardiovascular system to establish vessel patency, prevention of thrombosis, and the further prevention of restenosis after angioplasty. In contrast to many of the stents discussed below having metallic struts intruding into the blood flow in the vessel lumen which generate turbulence and create blood stasis points initiating thrombus formation, the smooth, continuous surface provided by the preferred tubular collagen-based inner conduit of our invention provides a hemodynamically superior surface for blood flow. the stent and stent-graft may also be employed in any body cavity, opening, or lumen where a device such as is described here is appropriate.

The absence of gaps or holes in the graft structure between stent struts of our invention allows the tacking of both large and small flaps and tears in the vessel wall. These flaps disrupt blood flow and attract thrombus. The disruption of the natural anti-thrombotic covering of endothelium only worsens the condition. When collagen-based materials are used, the collagen-based barrier interposed between blood and a disrupted or injured portion of the vessel wall serves to mask injured intimal or medial layers from blood, thereby preventing thrombus formation and intimal proliferation which may lead to restenosis.

The stent-graft acts as a mechanical barrier preventing tissue from proliferating into or impinging the lumen. The nature of the bioactivity of the collagen and the smoother flow characteristics at the blood-contacting surface are conducive to endothelial cell attachment and growth thereby assuring the long-term blood compatibility of the device.

Mechanically, the preferred stent structures (described in U.S. patent application Ser. Nos. 08/221,815 and 08/222,263 both filed on Apr. 1, 1994 by Lau et al, the entirety of which are incorporated by reference) provide a good combination of radial strength and flexibility. The preferred stent structures are also radially resilient and may be completely crushed or flattened and yet spring open again once the obstructive loading is removed. This ability is important for use in exposed portions of the body around the peripheral vasculature or around joints. The stent-graft can sustain a crushing traumatic blow or compression from the bending of a joint and still return to the open configuration once the load is removed.

With regard to delivery, the inventive self-expansion mechanism and procedure eliminates the need for a balloon catheter and the associated balloon rupture problems often associated with balloons. In addition, the absence of the bulk of the balloon allows a smaller delivery profile to be achieved. Unlike some other self-expanding stent designs, this stent-graft maintains a constant length throughout the expansion process. Thus, the stent-graft would not have some of the positioning problems associated with other many self-expanding stents. In treating longer lesions, our self-expanding design eliminates the need for special long balloons or repositioning of the balloon between inflations in order to expand the entire length of the stent.

Stents

The stents currently described in the open literature include a wide variety of different shapes.

Wallsten, U.S. Pat. No. 4,655,771, suggests a vascular prosthesis for transluminal implantation which is made up of a flexible tubular body having a diameter that is varied by adjusting the axial separation of the two ends of the body relative to each other. In general, the body appears to be a woven device produced of various plastics or stainless steel.

U.S. Pat. No. 4,760,849, to Kroph, shows the use of a ladder-shaped coil spring which additionally may be used as a filter in certain situations.

Porter, U.S. Pat. No. 5,064,435, suggests a stent made up of two or more tubular stent segments which may be deployed together so to produce a single axial length by a provision of overlapping areas. This concept is to permit the use of segments of known length, which, when deployed, may be used together in overlapping fashion additively to provide a stent of significant length.

Quan-Gett, U.S. Pat. No. 5,151,105, discloses an implantable, collapsible tubular sleeve apparently of an outer band and an inner spring used to maintain the sleeve in a deployed condition.

Wall, U.S. Pat. No. 5,192,307, suggests a stent having a number of holes therein and which is expandable using an angioplasty balloon so to allow ratchet devices or ledges to hold the stent in an open position once it is deployed.

Gianturco, in U.S. Pat. Nos. 4,580,568 and 5,035,706, describes stents formed of stainless steel wire arranged in a closed zigzag pattern. The stents are compressible to a reduced diameter for insertion into and removal from a body passageway. The stents appear to be introduced into the selected sites by discharge of the collapsed zigzag wire configuration from the tip of a catheter.

U.S. Pat. Nos. 4,830,003 and 5,104,404, to Wolff et al. shows a stent of a zigzag wire configuration very similar in overall impression to the Gianturco device. However, the stent is said to be self-expanding and therefore does not need the angioplasty balloon for its expansion.

Hillstead, U.S. Pat. No. 4,856,516, suggests a stent for reinforcing vessel walls made from a single elongated wire. The stent produced is cylindrical and is made up of a series of rings which are, in turn, linked together by half-hitch junctions produced from the single elongated wire.

Wiktor, U.S. Pat. Nos. 4,649,992, 4,886,062, 4,969,458, and 5,133,732, shows wire stent designs using variously a zigzag design or, in the case of Wiktor '458, a helix which winds back upon itself. Wiktor '062 suggests use of a wire component made of a low-memory metal such as copper, titanium or gold. These stents are to be implanted using a balloon and expanded radially for plastic deformation of the metal.

Wiktor '458 is similarly made of low-memory alloy and is to be plastically deformed upon its expansion on an angioplasty balloon.

Wiktor '732 teaches the use of a longitudinal wire welded to each turn of the helically wound zig-zag wire which is said to prevent the longitudinal expansion of the stent during deployment. A further variation of the described stent includes a hook in each turn of the helix which loops over a turn in an adjacent turn.

WO93/13825, to Maeda et al, shows a self-expanding stent similar to the Gianturco, Wolff, and Wiktor designs, formed of stainless steel wire, which is built into an elongated zig-zag pattern, and helically wound about a central axis to form a tubular shape interconnected with a filament. The bends of the helix each have small loops or "eyes" at their apexes which are inter-connected with a filament. Because of the teaching to connect the eyes of the apexes, the stent appears to be a design that axially expands during compression and may tear attached grafts because of the relative change in position of the arms of the zig-zag during compression of the stent.

MacGregor, U.S. Pat. No. 5,015,253, shows a tubular non-woven stent made up of a pair of helical members which appear to be wound using opposite "handedness". The stent helices desirably are joined or secured at the various points where they cross.

Pinchuk, in U.S. Pat. Nos. 5,019,090, 5,092,877, and 5,163,958, suggests a spring stent which appears to circumferentially and helically wind about as it is finally deployed except, perhaps, at the very end link of the stent. The Pinchuk '958 patent further suggests the use of a pyrolytic carbon layer on the surface of the stent to present a porous surface of improved antithrombogenic properties. The helices are not linked to each other, however, nor is there any suggestion that the helices be maintained in a specific relationship either as deployed or as kept in the catheter prior to deployment.

U.S. Pat. No. 5,123,917, to Lee, suggests an expandable vascular graft having a flexible cylindrical inner tubing and a number of "scaffold members" which are expandable, ring-like, and provide circumferential rigidity to the graft. The scaffold members are deployed by deforming them beyond their plastic limit using, e.g., an angioplasty balloon.

Tower, in U.S. Pat. Nos. 5,161,547 and 5,217,483, shows a stent formed from a zig-zag wire wound around a mandrel in a cylindrical fashion. It is said to be made from "a soft platinum wire which has been fully annealed to remove as much spring memory as possible." A longitudinal wire is welded along the helically wound sections much in the same way as was the device of Wiktor.

There are a variety of disclosures in which super-elastic alloys such as nitinol are used in stents. See, U.S. Pat. Nos. 4,503,569, to Dotter; 4,512,338, to Balko et al.; 4,990,155, to Wilkoff; 5,037,427, to Harada, et al.; 5,147,370, to-MacNamara et al.; 5,211,658, to Clouse; and 5,221,261, to Termin et al. None of these references suggest a device having discrete, individual, energy-storing torsional members as are required by this invention.

Jervis, in U.S. Pat. Nos. 4,665,906 and 5,067,957, describes the use of shape memory alloys having stress-induced martensite properties in medical devices which are implantable or, at least, introduced into the human body.

Stent-Grafts

A variety of stent-graft designs are shown in the following literature.

Perhaps the most widely known such device is shown in Ersek, U.S. Pat. No. 3,657,744. Ersek shows a system for deploying expandable, plastically deformable stents of metal mesh having an attached graft through the use of an expansion tool.

Palmaz describes a variety of expandable intraluminal vascular grafts in a sequence of patents: U.S. Pat. Nos.

4,733,665; 4,739,762; 4,776,337; and 5,102,417. The Palmaz '665 patent suggests grafts (which also function as stents) that are expanded using angioplasty balloons. The grafts are variously a wire mesh tube or of a plurality of thin bars fixedly secured to each other. The devices are installed, e.g., using an angioplasty balloon and consequently are not seen to be self-expanding.

The Palmaz '762 and '337 patents appear to suggest the use of thin-walled, biologically inert materials on the outer periphery of the earlier-described stents.

Finally, the Palmaz '417 patent describes the use of multiple stent sections each flexibly connected to its neighbor.

Rhodes, U.S. Pat. No. 5,122,154, shows an expandable stent-graft made to be expanded using a balloon catheter. The stent is a sequence of ring-like members formed of links spaced apart along the graft. The graft is a sleeve of a material such as expanded a polyfluorocarbon, e.g., GORE-TEX or IMPRAGRAFT.

Schatz, U.S. Pat. No. 5,195,984, shows an expandable intraluminal stent and graft related in concept to the Palmaz patents discussed above. Schatz discusses, in addition, the use of flexibly-connecting vascular grafts which contain several of the Palmaz stent rings to allow flexibility of the overall structure in following curving body lumen.

Cragg, "Percutaneous Femoropopliteal Graft Placement", *Radiology,* vol. 187, no. 3, pp. 643–648 (1993), shows a stent-graft of a self-expanding, nitinol, zig-zag, helically wound stent having a section of polytetrafluoroethylene tubing sewed to the interior of the stent.

Cragg (European Patent Application 0,556,850) discloses an intraluminal stent made up of a continuous helix of zig-zag wire and having loops at each apex of the zig-zags. Those loops on the adjacent apexes are individually tied together to form diamond-shaped openings among the wires. The stent may be made of a metal such as nitinol (col. 3, lines 15–25 and col. 4, lines 42+) and may be associated with a "polytetrafluoroethylene (PTFE), dacron, or any other suitable biocompatible-material". Those biocompatible materials may be inside the stent (col. 3, lines 52+) or outside the stent (col. 4, lines 6+). The alignment of the wire and the way in which it is tied mandates that it expand in length as it is expanded from its compressed form.

Grafts

As was noted above, the use of grafts in alleviating a variety of vascular conditions is well known. Included in such known grafting designs and procedures are the following.

Medell, U.S. Pat. No. 3,479,670, discloses a tubular prothesis adapted to be placed permanently in the human body. It is made of framework or support of a synthetic fiber such as DACRON or TEFLON. The tube is said to be made more resistant to collapse by fusing a helix of a polypropylene monofilament to its exterior. The reinforced fabric tube is then coated with a layer of collagen or gelatin to render the tubing (to be used as an esophageal graft) impermeable to bacteria or fluids.

Sparks, in U.S. Pat. Nos. 3,514,791, 3,625,198, 3,710,777, 3,866,247, and 3,866,609, teach procedures for the production of various graft structures using dies of suitable shape and a cloth reinforcing material within the die. The die and reinforcement are used to grow a graft structure using a patient's own tissues. The die is implanted within the human body for a period of time to allow the graft to be produced. The graft is in harvested and implanted in another site in the patient's body by a second surgical procedure.

Braun, in U.S. Pat. No. 3,562,820, shows a biological prosthesis manufactured by applying onto a support of a biological tissue (such as serosa taken from cattle intestine) a collagen fiber paste. The procedure is repeated using multiple layers of biological tissue and collagen fiber paste until a multi-layer structure of the desired wall thicknesses is produced. The prosthesis is then dried and removed prior to use.

Dardik et al, U.S. Pat. No. 3,974,526, shows a procedure for producing tubular prostheses for use in vascular reconstructive surgeries. The prosthesis is made from the umbilical cord of a newly born infant. It is washed with a solution of 1 percent hydrogen peroxide and rinsed with Ringer's lactate solution. It is then immersed in a hyaluronidase solution to dissolve the hyaluronic acid coating found in the umbilical cord. The vessels are then separated from the cord and their natural interior valving removed by use of a tapered mandrel. The vessels are then tanned with glutaraldehyde. A polyester mesh support is applied to the graft for added support and strength.

Whalen, U.S. Pat. No. 4,130,904, shows a prosthetic blood conduit having two concentrically associated tubes with a helical spring between them. Curved sections in the tube walls help prevent kinking of the tube.

Ketharanathan, U.S. Pat. No. 4,319,363, shows a procedure for producing a vascular prosthesis suitable for use as a surgical graft. The prosthesis is produced by implanting a rod or tube in a living host and allowing collagenous tissue to grow on the rod or tube in the form of coherent tubular wall. The collagenous-implant is removed from the rod or tube and tanned in glutaraldehyde. The prosthesis is then ready for use.

Bell, U.S. Pat. No. 4,546,500, teaches a method for making a vessel prosthesis by incorporating a contractile agent such as smooth muscle cells or platelets into a collagen lattice and contracting the lattice around a inner core. After the structure has set, additional layers are applied in a similar fashion. A plastic mesh sleeve is desirably sandwiched between the layers or imbedded within the structure to provide some measure of elasticity.

Hoffman Jr. et al, U.S. Pat. No. 4,842,575, shows a collagen impregnated synthetic vascular graft. It is made of a synthetic graft substrate and a cross-linked collagen fibril. It is formed by depositing a aqueous slurry of collagen fibrils into the lumen of the graft and massaging the slurry into the pore structure of the substrate to assure intimate admixture in the interior. Repeated applications and massaging and drying is said further to reduce the porosity of the graft.

Alonoso, U.S. Pat. No. 5,037,377, is similar in overall content to the Hoffman Jr. et al patent discussed above except that, in addition to collagen fibers, soluble collagen is introduced into the fabric. A suitable cross-linking agent such as glutaraldehyde is used to bond adjacent collagen fibers to each other.

Slepian et al, U.S. Pat. No. 5,213,580, teaches a process described as "paving" or "stabilizing by sealing the interior surface of a body vessel or organ" by applying a biodegradable polymer such as a polycaprolactone. The polymer is made into a tubular substrate, placed in position, and patched into place.

Finally, there are known vascular grafts using collagenous tissue with reinforcing structure. For instance, Pinchuk, in U.S. Pat. Nos. 4,629,458 and 4,798,606, suggests the use of collagen with some other type of fibrous structure supporting the collagen as a biograft. Similarly, Sinofsky et al., U.S. Pat. No. 5,100,429, suggests a partially-cured, collagen-based material used to form a graft within a blood vessel.

Kreamer, U.S. Pat. No. 4,740,207, suggests a intraluminal graft made of a semi-rigid resilient tube, open along a seam extending from one end to the other, which is expanded within the vessel and which resulting larger diameter is maintained by use of a ledge at the longitudinal seam for catching the opposite side of the seam on the expanded graft.

Deployment Procedures

Since most stents are introduced into the human body and deployed using an angioplasty balloon, there is very little description of the methodology or devices used in deploying self-expanding stents in stent grafts. A typical example of such expandable stents and methods of implant is shown in Wiktor, U.S. Pat. No. 4,886,062, in which a low memory alloy such as specified stainless steels, titanium alloys, or 19–22 karat gold is deployed using a balloon.

More pertinent to the invention here are the deployment devices shown in two patents to Hillstead (U.S. Pat. Nos. 4,913,141 and 5,019,085). These patents show a stent delivery system in which a delivery catheter having a cylindrical wall is wrapped with a stent. The stent is one which is expandable upon release. At each end of the stent is a loop which engages a release wire extending from within the catheter. The release wire extends from one end of the stent to the other. By pulling the release wire through the interior of the deployment catheter, the distal end is first released, and upon further pulling the second end is released from the exterior of the catheter. The deployment catheter may then be removed from the interior of the vessel.

None of the cited references suggest the claimed procedures and devices.

SUMMARY OF THE INVENTION

This invention involves procedures for folding and also for delivering foldable stents or stent-grafts to a site within the human body. The delivery may be percutaneous and through or over an endovascular catheter or via use of an an endoscopic device through a body opening or via the use of surgical or other procedures. The preferred expandable stent structure utilizes torsional regions which allow it to be folded to a very small diameter prior to deployment. In some variations of the preferred stent structure, the torsional members have an undulating shape which may be helically deployed to form the stent's cylindrical shape. The undulating shape may be aligned to allow the shapes in adjacent turns of the helix to be in phase. The undulating shapes may be generally V-shaped, U-shaped, sinusoidal, or ovoid. Adjacent undulating shapes may be held in the phased relationship using a flexible linkage, often made of a polymeric material. The undulating torsional members do not have any means at (or near) the apex of the undulating shapes which would tend to constrict the movement of the flexible linkage during compression or bending of the stent. The stent is preferably made of a highly flexible, superelastic alloy such as nitinol, but may be of any suitable elastic material such as various of the medically accepted stainless steels. The stent structure may also be of a series of rings incorporating the torsional members, which rings may be axially linked.

The graft component used to complement the stent is tubular and may be made of a polymeric material which may, if desired, be reinforced with fibers of random, woven, roving, or wound configurations. The tubular member may be cast onto or otherwise attached or imbedded into or onto the stent structure. The stent-graft may be used to reinforce vascular irregularities and provide a smooth interior vascular surface, particularly within smaller vessels. Obviously the stent and stent-graft may be used in any other medical service where such devices are commonly employed.

The device used in deploying the stent or stent grafts employs one or more "slip lines" which, in turn, may be of any of a variety of forms. The slip lines may be threaded through the stent, through loops specifically included in the folded stent for this purpose; the slip lines may be direct or may be woven in such a way that they act as would "sack knots" in releasing the stent as the lines are unwoven.

BRIEF DESCRIPTION OF THE DRAWINGS

FIGS. 15A, 15C, and 15E show procedures for folding the stent-grafts. FIGS. 15B, 15D, and 15F show the corresponding folded stent-grafts.

FIGS. 16A–16C show a schematic procedure for deploying the stent-grafts using an external sleeve.

FIGS. 19A–19C show a schematic procedure for deploying the stent-grafts (as shown in FIGS. 17A–17C and 18A–18C) using a tether wire.

DESCRIPTION OF THE INVENTION

Figure 1A:
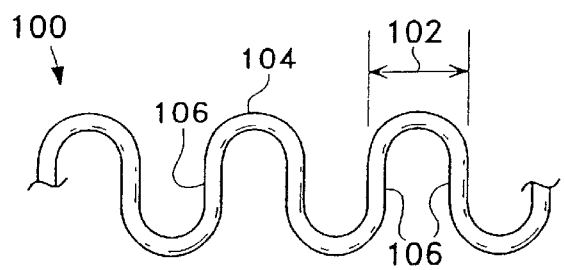
FIGS. 1A, 1B, 1C, 1D, and 1E are plan views of an unrolled stent form suitable for use in the invention.

As was noted above, this invention is a procedure for the folding and deployment of an expandable stent, a stent-graft, or a fiber- or filament-reinforced stent-graft. Also included in the invention is a stent or stent graft in combination with a slip-line. The stent-graft may be a combination of several components: a thin-walled tube generally coaxial with the stent, the expandable stent structure, and an optional network of fibers used to reinforce the tubular component. The expandable stent structure may be a cylindrical body produced of a helically placed (wound or otherwise preformed) torsion member having an undulating or serpentine shape or a series of axially situated rings comprising those torsion members. When the undulating torsion member is formed into the cylinder, the undulations may be aligned so that they are "in phase" with each other. The undulations are desirably linked, typically with a flexible linkage of a suitable polymeric or metallic material, to maintain the phased relationship of the undulations during compression and deployment. These stent configurations are exceptionally kink-resistant and flexible, particularly when flexed along the longitudinal axis of the stent.

When the stent is used in a reinforced stent-graft, that is to say: the stent is included into a thin-walled tube having reinforcing fibers, the fibers (or threads or filaments) may be formed into a network, such as a tubular mesh or otherwise reinforced with fibers of random, woven, roving, or wound configurations. The stent-graft may be delivered (perhaps, percutaneously through the vasculature) after having been folded to a reduced diameter. Once reaching the intended delivery site, it is expanded to form a lining on the vessel wall or cavity.

Methods of delivering the various devices using, among other devices, a percutaneous catheter and a slip line are also an aspect of the invention.

Stent Component

The materials typically used for vascular grafts, e.g., polytetrafluoroethylene (PTFE), collagen, etc. usually do not have the stiffness or strength by themselves both to stay open against the radial inward loads found in those vessels and to prevent their slippage from the chosen deployment site. In order to provide the strength required, a radially rigid stent structure may be incorporated into the stent-graft. The stent may be constructed of a reasonably high strength material, i.e., one which is resistant to plastic deformation when stressed. The structure is typically from one of three sources: 1.) a wire form in which a wire is first formed into an undulating shape and the resulting undulating shape is helically wound to form a cylinder, 2.) an appropriate shape is formed from a flat stock and wound into a cylinder, and 3.) a length of tubing is formed into an appropriate shape. These stent structures are typically oriented coaxially with the tubular graft component. The stent structures may be placed on the outer surface or the inner surface of the tubular member although it is often desirable that the stent be imbedded in the graft tubing wall for ease of integration with the tubing and to prevent the stent's exposure to blood. It is desired that the stent structure have the strength and flexibility to tack the graft tubing firmly and conformally against the vessel wall. In order to minimize the wall thickness of the stent-graft, the stent material should have a high strength-to-volume ratio. Use of designs described herein provides stents which are shorter in length than those often used in the prior art. Additionally, the designs do not suffer from a tendency to twist (or helically unwind) or to shorten as the stent is deployed. As will be discussed below, materials suitable in these stents and meeting these criteria include various metals and some polymers.

A stent-graft, whether percutaneously delivered with a catheter or delivered using surgical techniques, must expand from a reduced diameter, necessary for delivery, to a larger deployed diameter. The deployed diameters of these devices obviously vary with the size of the body lumen or cavity into which they are placed. For instance, the stents of this invention may range in size (for neurological applications) from 2.0 mm in diameter to 30 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Expansion ratios for use with the stents and stent-grafts of the invention typically are in the range of about 2:1 to about 4:1 although the invention is not so limited. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The stent-graft is fabricated in the expanded configuration. In order to reduce its diameter for delivery the stent-graft would be folded along its length, similar to the way in which a PCTA balloon would be folded. It is desirable, when using super-elastic alloys which also have temperature-memory characteristics, to reduce the diameter of the stent at a temperature below the transition-temperature of the alloys. Often the phase of the alloy at the lower temperature is somewhat more workable and easily formed. The temperature of deployment is desirably above the transition temperature to allow use of the super-elastic properties of the alloy.

As a generic explanation of the mechanical theory of the inventive stent, reference is made to FIGS. 1A, 1B, 1C, 1D, 1E, 2, 3, and 4. FIG. 1A is a plan view of an isolated section of a stent device suitable for use in the invention and is intended both to identify a suitable stent variation and to provide conventions for naming the components of the torsion member (100). FIG. 1A shows, in plan view, an undulating torsion member (100) formed from a wire stock into a U-shape. A torsion pair (102) is made up of an end member (104) and two adjacent torsion lengths (106). Typically, then, each torsion length (106) will be a component to each of its adjacent torsion pairs (102). The U-shaped torsion pair (102) may be characterized by the fact that the adjacent torsion lengths are generally parallel to each other prior to formation into the stent.

The depicted stents use undulating torsion members which are "open" or "unconfined" at their apex or end member (104). By "open" or "unconfined" is meant that the apex or end member (104) does not have any means in that apex which would tend to inhibit the movement of the flexible linkage (discussed below) down between the arms or torsion lengths (106) of the torsion pair (102).

Figure 1B:
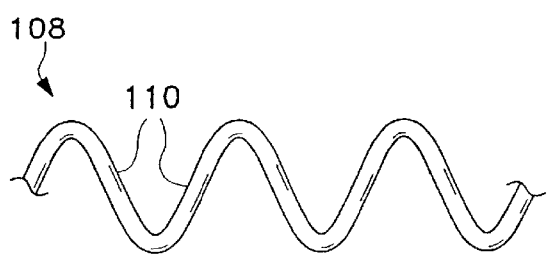

FIG. 1B shows another variation of the stent having a sinusoidal shaped torsion member (108). In this variation, the adjacent torsion lengths (110) are not parallel and the wire forms an approximate sine shape before being formed into a cylinder.

Figure 1C:
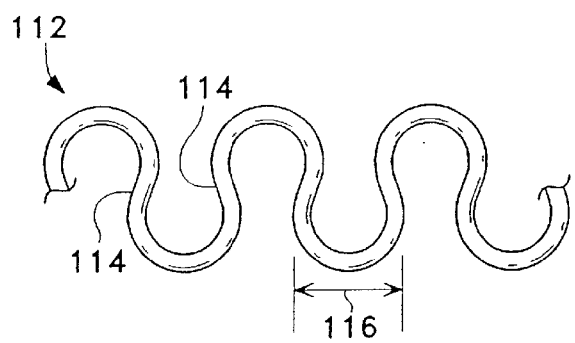

FIG. 1C shows a variation having an ovoid shaped torsion member (112). In this variation, the adjacent torsion lengths (114) are again not parallel. The wire forms an approximate open-ended oval with each torsion pair (116) before being formed into a cylinder.

Figure 1D:
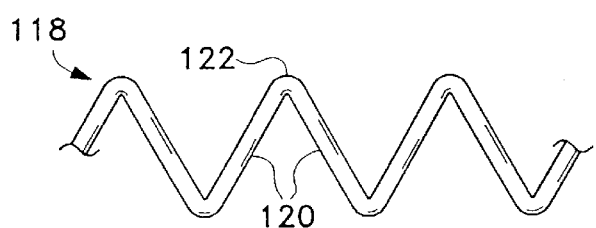

FIG. 1D shows another variation having a V-shaped torsion member (118). In this variation, the adjacent torsion lengths (120) form a relatively sharp angle at the torsion end (122) shape before being formed into a cylinder.

Figure 1E:
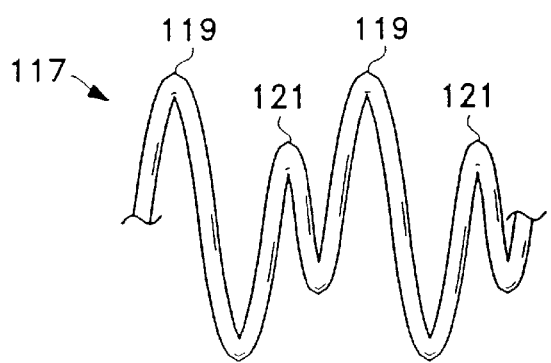

FIG. 1E shows a variation in which adjacent torsion members on the stent (117) have differing amplitude. The peaks of the high amplitude torsion members (119) may be lined up "out of phase" or "peak to peak" with short amplitude (121) or high amplitude torsion members in the adjacent turn of the helix or may positioned "in phase" similar to those discussed with regard to FIG. 2 below.

The configurations shown in FIGS. 1A–1E are exceptionally kink-resistant and flexible when flexed along the longitudinal axis of the stent.

As ultimately deployed, a section of the torsion member found on one of FIGS. 1A–1E would be helically wound about a form of an appropriate size so that the end members (e.g., 104 in FIG. 1A) would be centered between the end members of the torsion member on an adjacent turn of the helix. This is said to be "in phase". "Out of phase" would be the instance in which the adjacent members meet directly, i.e., end member-to-end member. In any event, once so aligned, the phasic relationship may be stabilized by weaving a flexible linkage through the end members from one turn of the helix to the next.

Figure 2:
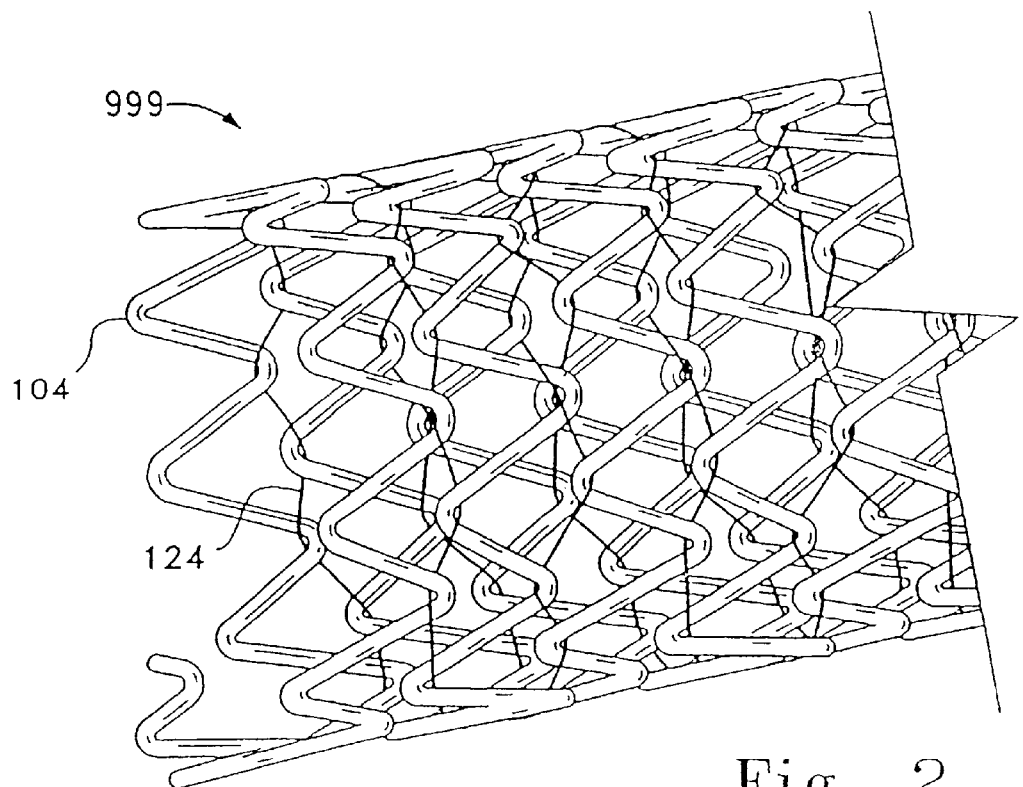
FIG. 2 is a side view of the a stent as shown in FIGS. 1A–1E.

FIG. 2 shows a side view of a typical stent (999) made according to this invention including the phased relationship of the helical turns of the stent and the flexible linkage (124).

Figure 3:
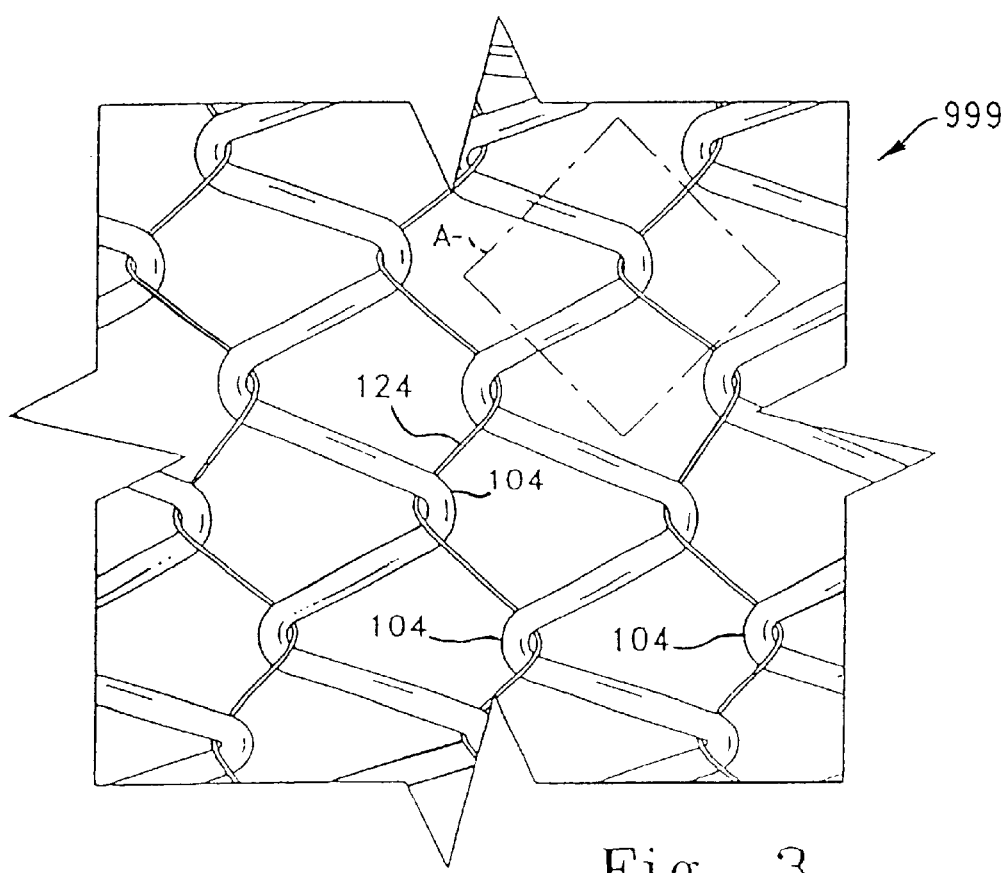
FIG. 3 is a close-up of a portion of the stent shown in FIG. 2.

FIG. 3 shows a close-up of the FIG. 2 stent and depicts the phased relationship (within box A) and shows in detail a typical way in which the flexible linkage (124) is looped through the various end members (104) to maintain the phased relationship. It may be noted that the flexible linkage (124) is free to move away from the apex at the end members (104) without constraint.

Figure 4:
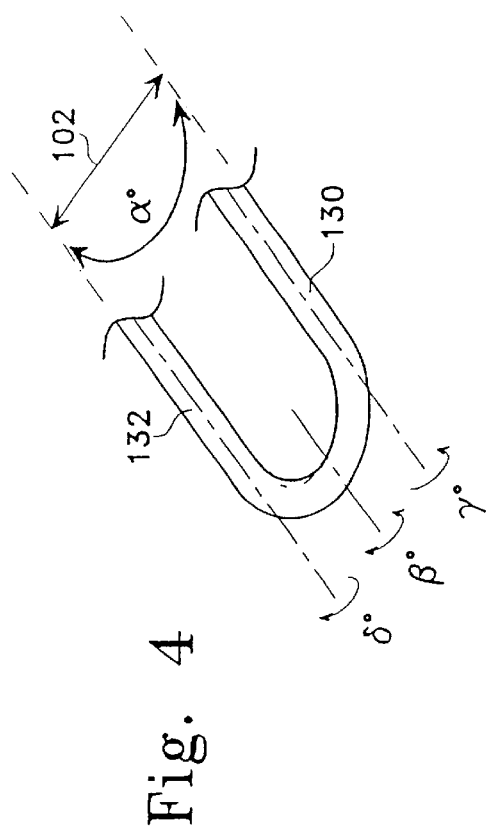
FIG. 4 is an abstracted portion of a suitable stent and shows the concept of torsion on a portion of that stent.

The stent may be folded in some fashion (as will be discussed below) for deployment. During the step of folding, the stent undergoes a transformation. FIG. 4 shows an isolated torsion pair (102). When the torsion pair (102) undergoes a flexing in the amount of $\alpha°$, the end member will flex some amount $\beta°$, torsion length (130) will undertake a twist of $\gamma°$, and torsion length (132) will undertake a twist opposite of that found in torsion length (130) in the amount of $\delta°$. The amounts of angular torsion found in the torsion lengths (130 and 132) will not necessarily be equal because the torsion lengths are not necessarily at the same angle to the longitudinal axis of the stent. Nevertheless, the sum of $\beta°+\gamma°+\delta°$ will equal $\alpha°$. When a value of $\alpha°$ is chosen, as by selection of the shape and size of the stent upon folding, the values of the other three angles ($\beta°,\gamma°,\delta°$) are chosen by virtue of selection of number of torsion pairs around the stent, size and physical characteristics of the wire, and length of the torsion lengths (130 and 132). Each of the noted angles must not be so large as to exceed the values at which the chosen material of construction plastically deforms at the chosen value of $\alpha°$.

To further explain: it should be understood that the torsion pair (102) undergoes a significant amount of flexing as the stent is folded or compressed in some fashion. The flexing provides a twist to the torsion lengths, (130 and 132), a significant portion of which is generally parallel to the longitudinal axis of the stent. It is this significant imposed longitudinal torsion which forms an important concept of the desired stent.

As noted elsewhere, in one very desirable variation of the stent, as deployed in FIGS. 2 and 3, the stent is folded longitudinally and is delivered through the lumen of the catheter in such a way that it is self-restoring once it has been introduced to the selected body lumen site.

With that preliminary background in place, it should be apparent that a simple tube of metal will undergo plastic deformation when sufficient force is applied radially to the outside of the tube. The amount of force needed to cause that plastic deformation will depend on a wide variety of factors, e.g., the type of metal utilized in the tube, the width of the tube, the circumference of the tube, the thickness of the material making up the band, etc. The act of attempting to fold a tube along its centered axis in such a way to allow it to pass through a lumen having the same or smaller diameter and yet maintain the axis of the folded stent parallel to the axis of the lumen-invites plastic deformation in and of the stent.

The described stent uses concepts which can be thought of as widely distributing and storing the force necessary to fold the tubular stent into a configuration which will fit through a diameter smaller than its relaxed outside diameter without inducing plastic deformation of the constituent metal or plastic and yet allowing those distributed forces to expand the stent upon deployment.

Once the concept of distributing the folding or compression stresses both into a bending component (as typified by angle $\beta°$ in FIG. 4) and to twisting components (as typified by angle $\gamma°$ and $\delta°$ in FIG. 4), and determining the overall size of a desired stent, determination of the optimum materials as well as the sizes of the various integral components making up the stent becomes straightforward. Specifically, the diameter and length of torsion lengths (130 and 132) and end sector (104), the number of torsion pairs (102) around the stent may then be determined.

Figure 5:
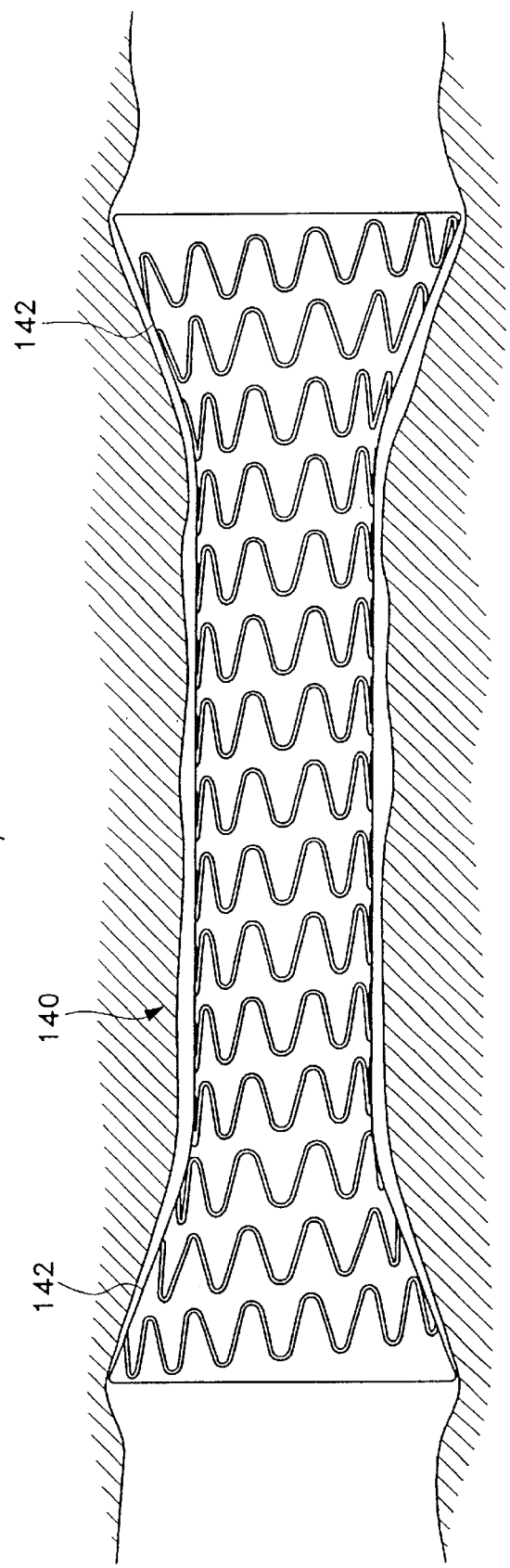
FIG. 5 is a side view of the inventive stent showing a variation having flared ends.

FIG. 5 shows, in side view, a variation of the stent (140) made from wire having flares (142) at one or both ends. The flaring provides a secure anchoring of the stent or stent-graft (140) against the vessel wall. This prevents the implant from migrating downstream. In addition, the flaring provides a tight seal against the vessel so that the blood is channelled through the lumen rather than outside the graft. The undulating structure may vary in spacing to allow the helix turns to maintain its phased relationship between turns of the helix and to conform to the discussion just above. A flexible linkage between the contiguous helical turns may also be applied to at least a portion of the helices.

Figure 6:
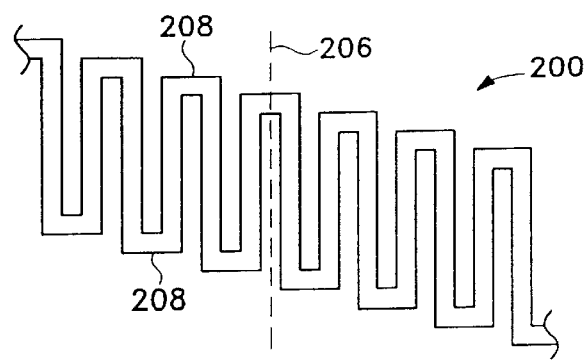
FIGS. 6, 7, and 8 show plan views of an unrolled stent produced from flat stock.
Figure 7:
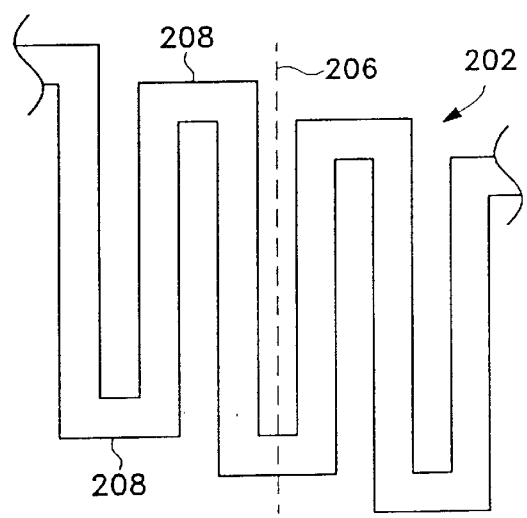
Figure 8:
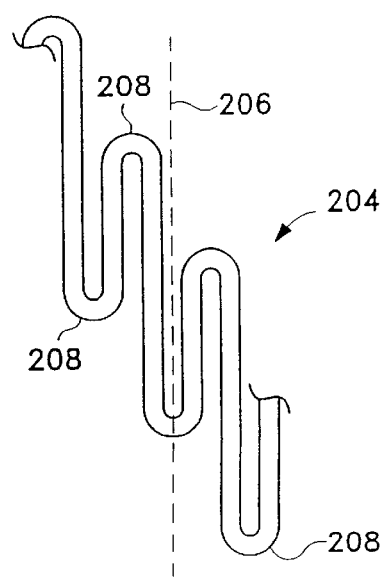
Figure 9:
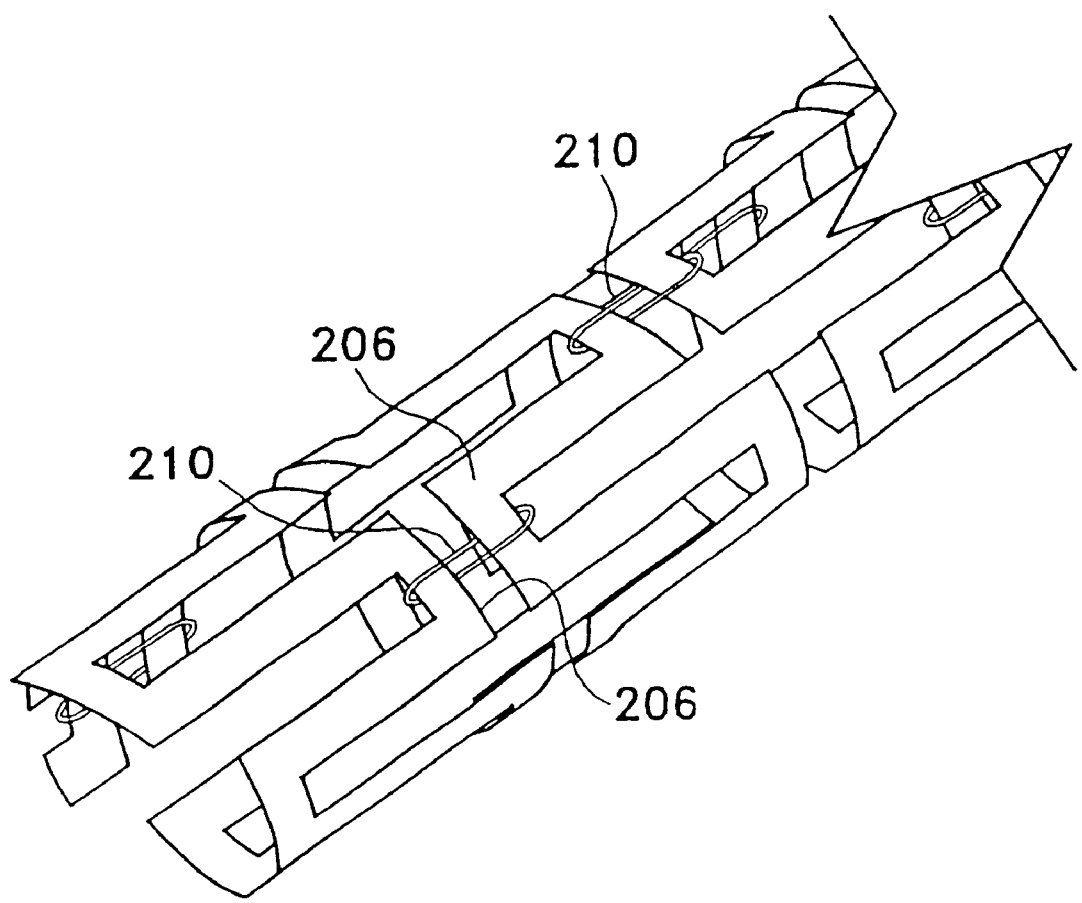
FIG. 9 shows a quarter view of the rolled stent using the flat stock pattern shown in FIG. 7.

The stent structure may also be made by forming a desired structural pattern out of a flat sheet. The sheet may then be rolled to form a tube. FIGS. 6, 7, and 8 show plan views of torsion members (respectively 200, 202, and 204) which may be then rolled about an axis (206) to form a cylinder. As is shown in FIG. 9, the end caps (208) may be aligned so that they are "out of phase". The flexible linkage (210) is then included to preserve the diameter of the stent.

The stent shown in FIG. 9 may be machined from tubing. If the chosen material is nitinol, careful control of temperature during the machining step may be had by EDM (electro-discharge-machining), laser cutting, chemical machining, or high pressure water cutting.

Figure 10:
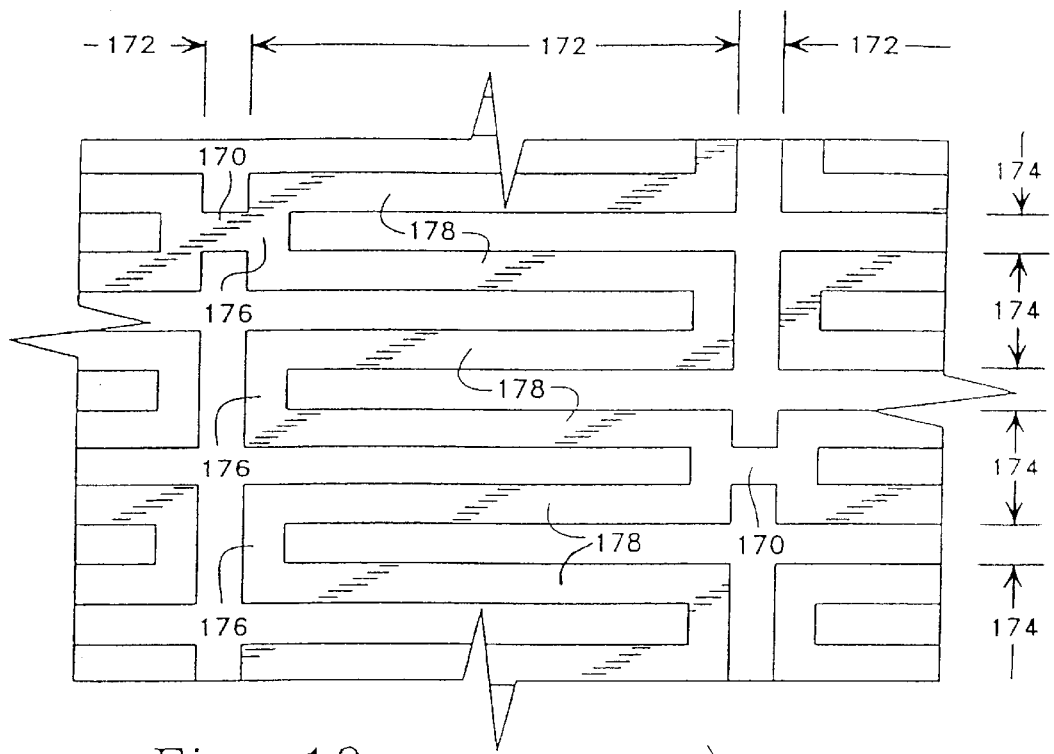
FIG. 10 shows a plan view of an unrolled stent produced from flat stock having a ringed structure.

FIG. 10 is a conceptual schematic of an isolated ring section of another variation of the stent component useful in this invention. The FIG. 10 is intended only to identify and to provide conventions for naming the components of the ring. FIG. 10 shows, in plan view, the layout of the various components of a ring as if they were either to be cut from a flat sheet and later rolled into tubular formation for use as a stent with welding or other suitable joining procedures taking place at the seam or (if constructed from tubing) the layout as if the tubing was cut open. The portion of the stent between tie members (170) is designated as a ring (172) or ring section. Tie members (170) serve to link one ring (172) to an adjacent ring (172). A torsion pair (174) is made up of a cap member (176) and two adjacent torsion members (178). Typically, then, each torsion member (178) will be a component to each of its adjacent torsion pairs (174).

Figure 11:
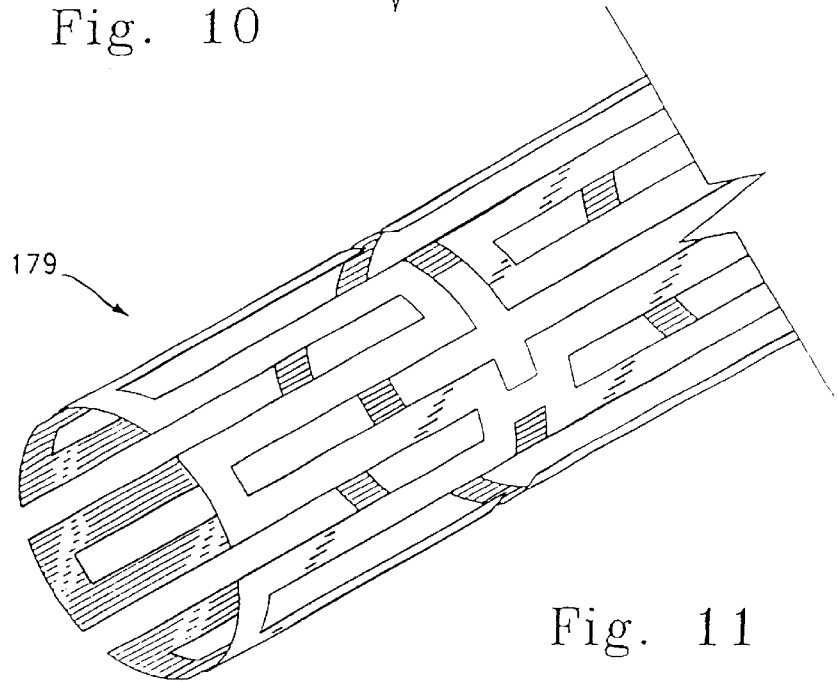
FIG. 11 shows a front quarter view of the rolled ring structured stent using the flat stock pattern shown in FIG. 9.

As ultimately deployed, a roll of the sheet found in FIG. 10 would be entered into the body lumen. Typically, it would be folded in some fashion which will be discussed below. A front quarter perspective view of the rolled stent (179) is shown in the FIG. 11.

Figure 12:
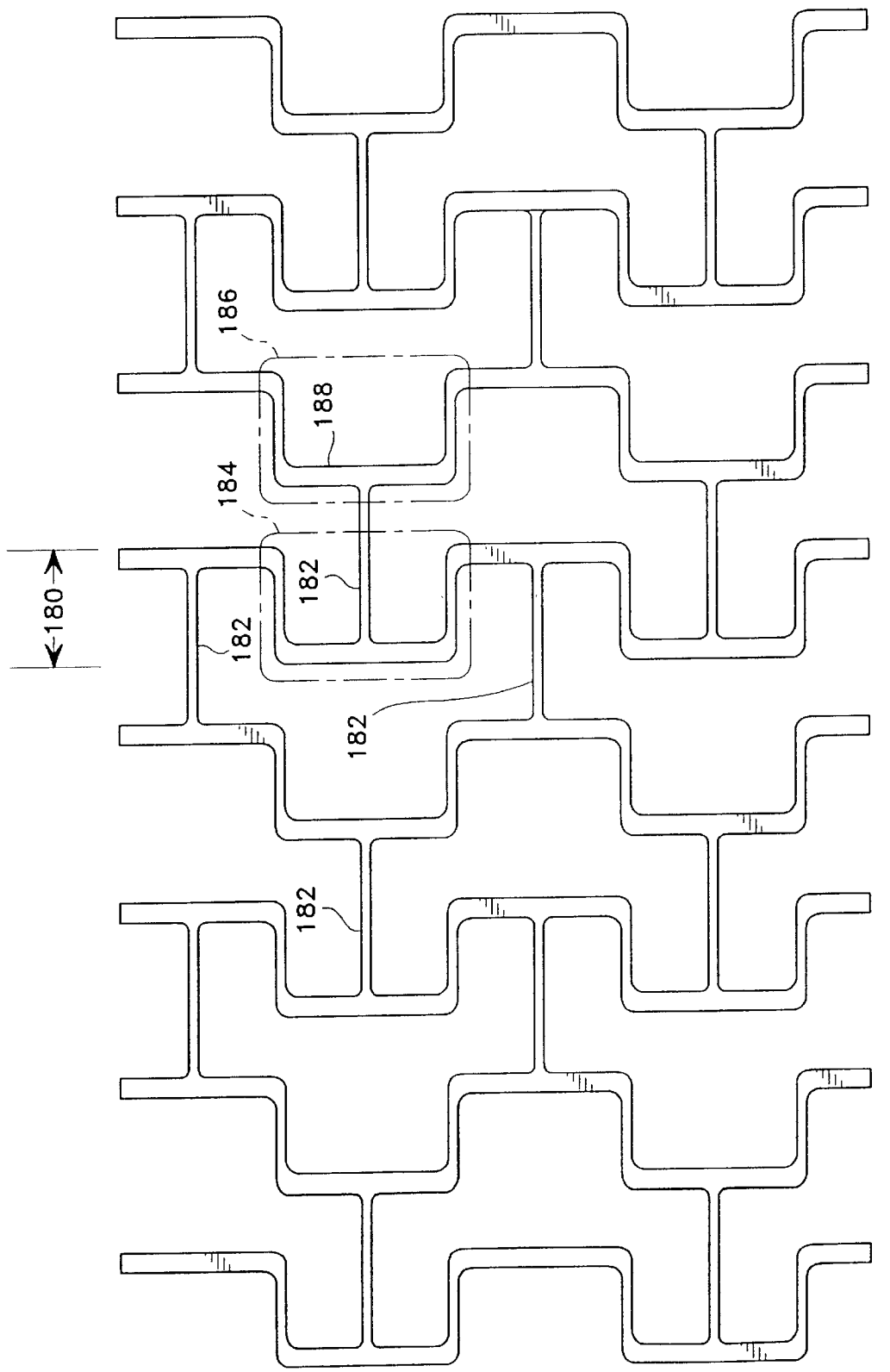
FIGS. 12, 13, and 14 show plan views of variations of unrolled stents useful in this invention.

FIG. 12 shows a variation of the stent having a ring section (180) similar in configuration to that shown above and joined by tie members (182). Those tie members (182) extend from the inside of a torsion pair (184) to the outside of a torsion pair (186) in the adjacent ring section. The tie members (182) experience no twisting because of their placement in the middle of end cap (188). The tie members may be offset on the end cap, if so desired, to allow the tie members to accept some of the twisting duty.

Figure 13:
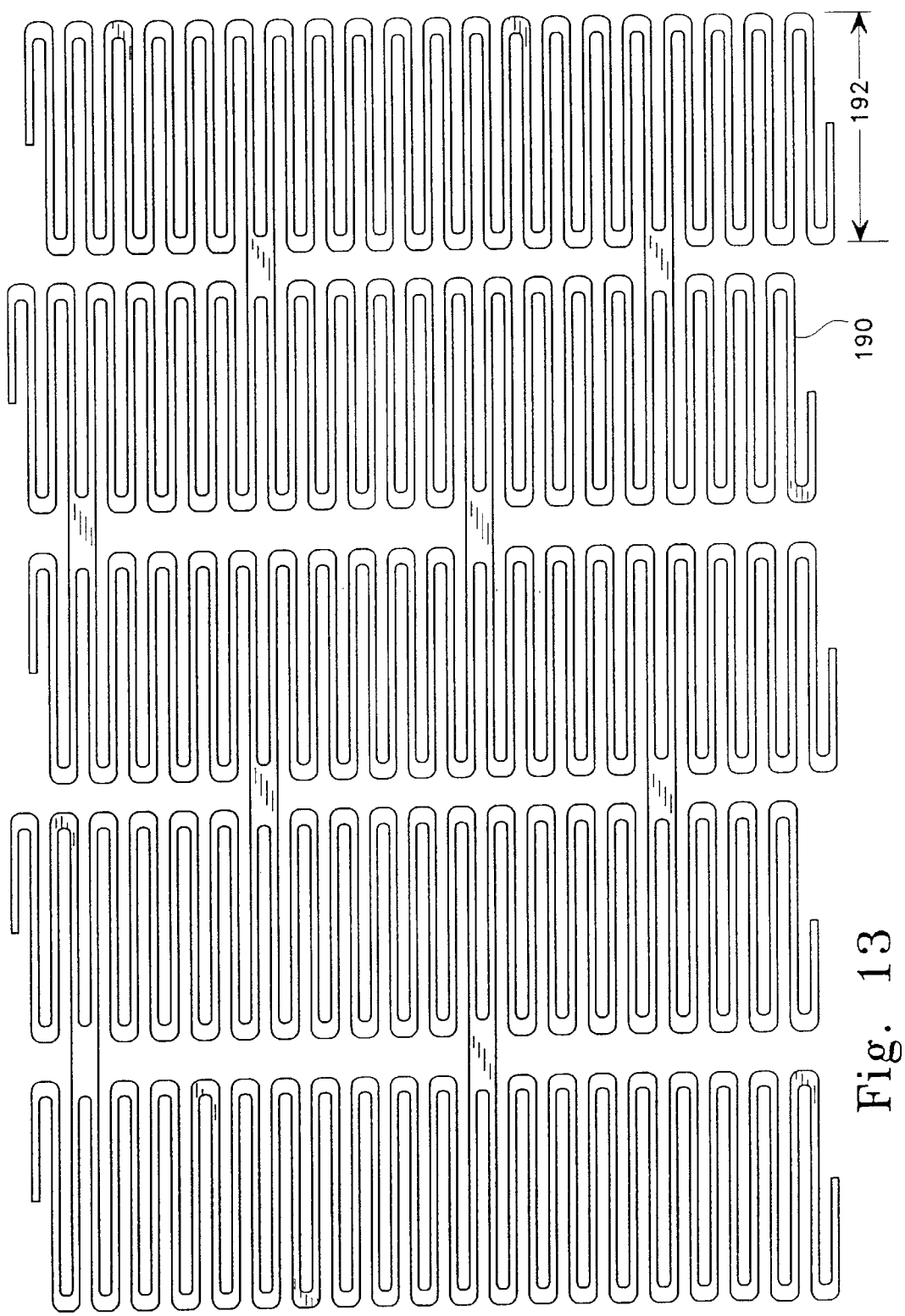

FIG. 13 shows a plan view of a variation of the inventive stent in which the number of torsion members (190) in a selected ring member (192) is fairly high. This added number of torsion members may be due to a variety of reasons. For instance, the material of construction may have a significantly lower tolerance for twisting than the materials in those prior Figures. Adding more torsion bars lessens the load carried on each of the several bars. Alternatively, for the same material, the stent may need be folded to a smaller diameter for deployment than those earlier variations.

Figure 14:
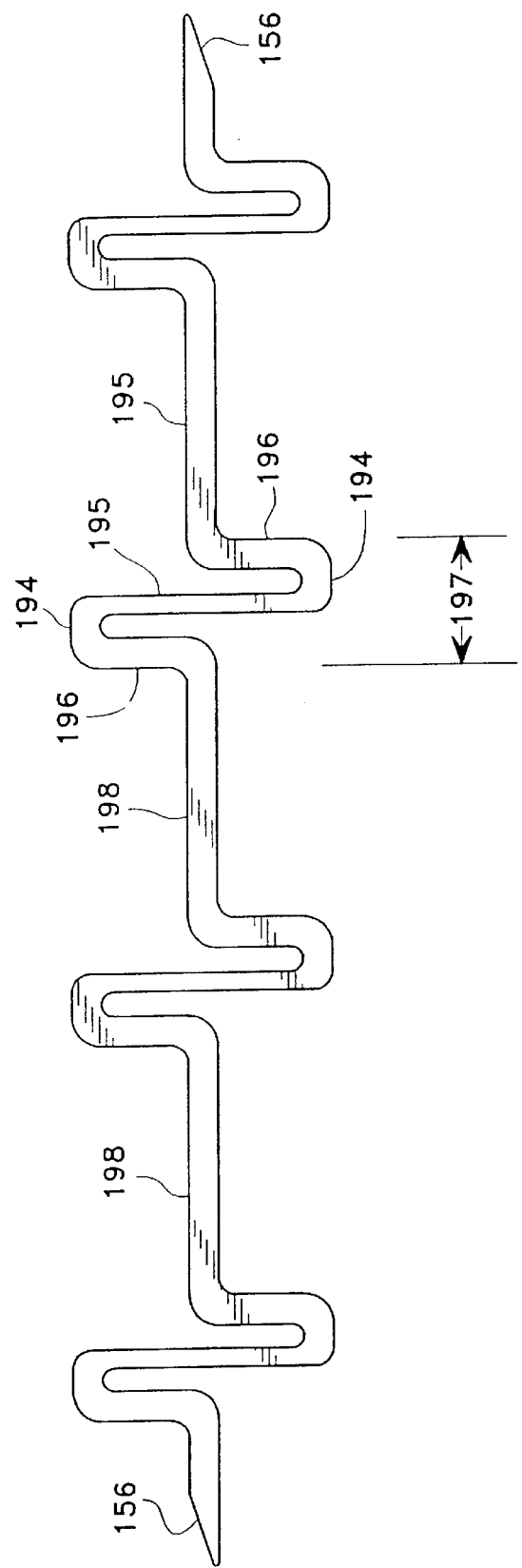
Figure 17C:
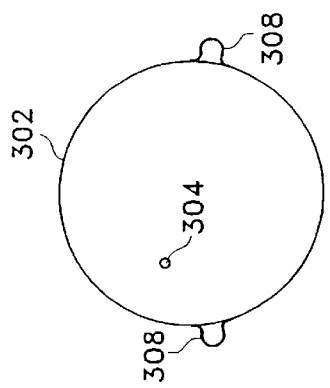
FIGS. 17B, 17C, 18B, and 18C show end views of the folded stent and of the open stent shown respectively in FIGS. 17A and 18A.

FIG. 14 shows a variation of the invention in which the end caps (194) are bound by a long torsion member (195) and two short torsion members (196). This torsion set (197) is in turn separated from the adjacent torsion set (197) by a bridge member (198) which shares the bending load of the stent when the stent is rolled and the ends (199) joined by, e.g., welding. The torsion members (196) have a greater width than that of the long torsion member (195) so as to balance the load around the ring during deformation and thereby to prevent the bridge members from becoming askew and out of the ring plane.

It should be clear that a variety of materials variously metallic, super-elastic alloys, and preferably nitinol, are suitable for use in these stents. Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY), platinum/tungsten alloys, various titanium alloys, and especially the nickel-titanium alloys generically known as "nitinol".

Nitinol is especially preferred because of its "super-elastic" or "pseudo-elastic" shape recovery properties, i.e., the ability to withstand a significant amount of bending and flexing and yet return to its original form without deformation. These metals are characterized by their ability to be transformed from an austenitic crystal structure to a stress-induced martensitic structure at certain temperatures, and to return elastically to the austenitic shape when the stress is released. These alternating crystalline structures provide the alloy with its super-elastic properties. These alloys are well known but are described in, U.S. Pat. Nos. 3,174,851, 3,351,463, and 3,753,700. Typically, nitinol will be nominally 50.6% (±0.2%) Ni with the remainder Ti. Commercially available nitinol materials usually will be sequentially mixed, cast, formed, and separately cold-worked to 30–40%, annealed, and stretched. Nominal ultimate yield strength values for commercial nitinol are in the range of 30 psi and for Young's modulus are about 700 kBar.

The '700 patent describes an alloy containing a higher iron content and consequently has a higher modulus than the Ni—Ti alloys. Nitinol is further suitable because it has a relatively high strength to volume ratio. This allows the torsion members to be shorter than for less elastic metals. The flexibility of the stent-graft is largely dictated by the length of the torsion member components in the stent structural component. The shorter the pitch of the device, the more flexible the stent-graft structure can be made. Materials other than nitinol are suitable. Spring tempered stainless steels and cobalt-chromium alloys such as ELGILOY are also suitable as are a wide variety of other known "super-elastic" alloys.

Although nitinol is preferred in this service because of its physical properties and its significant history in implantable medical devices, we also consider it suitable for use as a stent because of its overall compatibility with magnetic resonance imaging (MRI) technology. Many other alloys, particularly those based on iron, are an anathema to the practice of MRI causing exceptionally poor images in the region of the alloy implant. Nitinol does not cause such problems.

Other materials suitable as the stent include certain polymeric materials, particularly engineering plastics such as thermotropic liquid crystal polymers ("LCP's"). These polymers are high molecular weight materials which can exist in a so-called "liquid crystalline state" where the material has some of the properties of a liquid (in that it can flow) but retains the long range molecular order of a crystal. The term "thermotropic" refers to the class of LCP's which are formed by temperature adjustment. LCP's may be prepared from monomers such as p,p'-dihydroxy-polynuclear-aromatics or dicarboxy-polynuclear-aromatics. The LCP's are easily formed and retain the necessary interpolymer attraction at room temperature to act as high strength plastic artifacts as are needed as a foldable stent. They are particularly suitable when augmented or filled with fibers such as those of the metals or alloys discussed below. It is to be noted that the fibers need not be linear but may have some performing such as corrugations which add to the physical torsion enhancing abilities of the composite.

The flexible linkage between adjacent turns of the helix (124 in FIGS. 2 and 3) may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred is the use of polymeric biocompatible filaments. Synthetic polymers such as polyethylene, polypropylene, polyurethane, polyglycolic acid, polyesters, polyamides, their mixtures, blends, copolymers, mixtures, blends and copolymers are suitable; preferred of this class are polyesters such as polyethylene terephthalate including DACRON and MYLAR and polyaramids such as KEVLAR, polyfluorocarbons such as polytetrafluoroethylene with and without copolymerized hexafluoropropylene (TEFLON or GORETEX), and porous or nonporous polyurethanes. Natural materials or materials based on natural sources such as collagen are especially preferred in this service.

Tubular Component

The tubular component or member of the stent-graft may be made up of any material which is suitable for use as a graft in the chosen body lumen. For instance, natural material may be introduced onto the inner surface of the stent and fastened into place. Synthetic polymers such as polyethylene, polypropylene, polyurethane, polyglycolic acid, polyesters, polyamides, their mixtures, blends, copolymers, mixtures, blends and copolymers are suitable; preferred of this class are polyesters such as polyethylene terephthalate including DACRON and MYLAR and polyaramids such as KEVLAR, polyfluorocarbons such as polytetrafluoroethylene with and without copolymerized hexafluoropropylene (TEFLON or GORETEX), and porous or nonporous polyurethanes. Other especially preferred materials include the expanded fluorocarbon polymers (especially PTFE) materials described in British. Pat. Nos. 1,355,373, 1,506,432, or 1,506,432 or in U.S. Pat. Nos. 3,953,566, 4,187,390, or 5,264,276, the entirety of which are incorporated by reference.

Collagen is easily formed into thin-walled tubes which are limp, compliant, flexible, uniform, and have smooth surfaces. The tubing walls may have a hydrated thickness of 0.001 to 0.020 inches (or to 0.100 inches in some cases) for efficacy. Other thicknesses may be used if specific goals are to be achieved. They form non-thrombogenic surfaces which will support the growth of endothelium.

Highly preferred materials are certain collagen-based materials of COLLAGEN CORPORATION of Palo Alto, Calif. One such desired collagen composition is a pharmaceutically acceptable non-immunogenic composition formed by covalently binding atelopeptide collagen to pharmaceutically pure, synthetic, hydrophilic polymers via specific types of chemical bonds to provide collagen/polymer conjugates as described in U.S. Pat. No. 5,162,430, to Rhee et al, and WO 94/01483 (PCT/US93/06292), the entirety of which are incorporated by reference.

Included in the class of preferred expanded fluoropolymers are polytetrafluoroethylene (PTFE), fluorinated ethylene propylene (FEP), copolymers of tetrafluoroethylene (TFE) and per fluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is expanded PTFE. The graft may adhere to or partially encapsulate or be cast about the stent when appropriate materials such as castable polyurethane or collagen-based materials are employed. When the stent-graft is produced in such a way that the openings in the stent contain graft material (as by casting), then we refer to such a stent-graft as an "integral stent-graft".

In a stent-graft, the graft tube acts as an intravascular blood conduit to line the interior surface of the blood vessel. It isolates the lined segment of the vessel from direct contact with blood flow, tacks any tears or dissections, helps reinforce the vessel wall to protect against or isolate aneurysms, and provides a smooth, relatively thin, conformal surface for the blood flow.

The tubular component may be reinforced using a network of small diameter fibers. The fibers may be random, braided, roving, knitted, or woven. The fibers may be imbedded in the tubular component wall, may be placed in a separate layer coaxial with the tubular component, or may be used in a combination of the two.

The fibrous material may also be mixed with or imbedded into the tubular layer and cast or injected around the stent. This fibrous material may extend for the length of the device or may be shorter. The fibers may be wound or placed in any reasonable orientation within the device. Alternatively, randomly oriented short segments of fibers may also be imbedded in the wall of the tubing. The fiber may be any suitable fibrous blood-compatible material including polyesters such as DACRON, polyamides such as NYLON, KEVLAR, polyglycolic acids, polylactic acids, polyethylene, polypropylene, silk or other strong flexible fiber which are not detrimentally affected in the medical service in which this device is placed. Specifically, polypropylene and the like will not be dissolved in blood but polyglycolic acid will dissolve. Each are suitable but work in different ways.

In addition, one or more radio-opaque metallic fibers, such as gold, platinum, platinum-tungsten, palladium, platinum-iridium, rhodium, tantalum, or alloys or composites of these metals like may be incorporated into the multi-strand reinforcement network to allow fluoroscopic visualization of the device.

In a polymer-fiber composite tube, the fibers carry much of the hoop stress and other loadings imposed by the vessel. This relieves the loading on the tube material, significantly increases the burst strength and fatigue properties of the tube, and otherwise helps to provide a smoother wrinkle-free inner lumen. In addition, this makes the tube more effective in hydraulically isolating the vessel and as a result prevents the formation or worsening of aneurysms. This would be particularly beneficial in thinned weakened vessel walls resulting from de-bulking interventions or from medial thinning that has been seen to accompany stent placement. Another benefit of the fiber reinforcement is the increase in resistance to radially inward loading, especially if the loading is very focussed. Finally, fiber reinforcement may also impart some longitudinal stiffness to the stent-graft. This allows the stent-graft to maintain its strength and prevent it from kinking or sagging into the lumen.

Deployment of the Invention

When a stent-graft having torsion members is folded, crushed, or otherwise collapsed, mechanical energy is stored in torsion in those torsion members. In this loaded state, the torsion members have a torque exerted about them and consequently have a tendency to untwist. Collectively, the torque exerted by the torsion members as folded down to a reduced diameter must be restrained from springing open. The stent typically has at least one torsion member per fold to take advantage of the invention. The stent-graft is folded along its longitudinal axis and restrained from springing open. The stent-graft is then deployed by removing the restraining mechanism, thus allowing the torsion members to spring open against the vessel wall.

The attending surgeon will choose a stent or stent-graft having an appropriate diameter. However, inventive devices of this type are typically selected having an expanded diameter of up to about 10% greater than the diameter of the lumen to be the site of the stent deployment.

FIG. 15A shows a sequence of folding the device (230) of this invention about a guidewire (232) into a loose C-shaped configuration. FIG. 15B shows a front quarter view of the resulting folded stent or stent-graft.

FIG. 15C shows a sequence of folding the device (230) of this invention about a guidewire (232) into a rolled configuration. FIG. 15D shows a front quarter view of the resulting folded stent or stent-graft.

FIG. 15E shows a sequence of folding the device (230) of this invention about a guidewire (232) into a triple lobed configuration. FIG. 15F shows a front quarter view of the resulting folded stent or stent-graft.

The stent-graft may be tracked through the vasculature to the intended deployment site and then unfolded against the vessel lumen. The graft component of the device, here depicted as a collagen tube, is limp, flexible, and thus easy to fold. Folding of the stent structure in the manner discussed above allows it to return to a circular, open configuration.

FIGS. 16A–16C show one desired way to place the devices of the present invention and allow them to self-expand. FIG. 16A shows a target site (246) having, e.g., a narrowed vessel lumen. A guidewire (248) having a guide tip (250) has been directed to the site using known techniques. The stent-graft (252) is mounted on guidewire tubing (254)

inside outer sliding sheath (256) after having folded in the manner discussed above. The outer sliding sheath (256) binds the compressed stent-graft (252) in place until released.

FIG. 16B shows placement of the stent-graft (252) at the selected site (246) by sliding the stent-graft (252) over the guidewire (248) all together with the guidewire tubing (254) and the outer sliding sheath (256). The stent-graft (252) is deployed by holding the guidewire tubing (254) in a stationary position while withdrawing the outer sliding sheath (256). The stent-graft (252) can be seen in FIG. 16B as partially deployed.

FIG. 16C shows the stent-graft (252) fully deployed after the guidewire tubing (254) and the outer sliding sheath (256) have been fully retracted.

FIGS. 17A–C, 18A–C, and 19A–C show an inventive variation of deploying a stent or stent-graft made according to this invention. These methods involve the use of a control line or tether line which maintains the stent or stent-graft in a folded configuration until release.

Figure 17B:
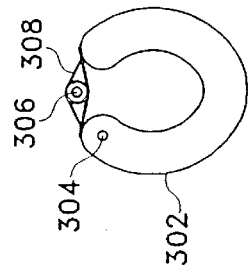
Figure 17A:
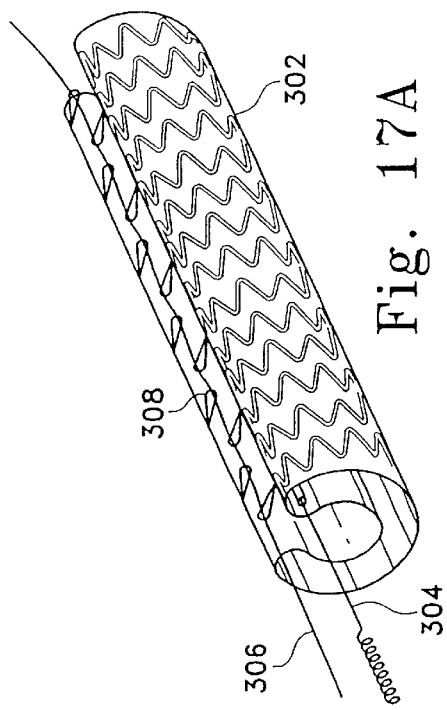
FIGS. 17A and 18A show front quarter views of folded stents or stent-grafts held in that folded position by a tether wire.

FIG. 17A is a front-quarter view of the stent (302) or stent-graft which has been folded as shown in the Figures discussed above. The stent (302) is folded about guidewire (304) so that, when deployed, the guidewire (304) is within the stent (302). Central to the variation shown here is the tether wire (306) which is passed through loops (308) associated with the various helices as they wind about the stent (302). The loops (308) may be formed from the flexible link (124 in FIGS. 2 or 3) or may be simply an alternating weave through (or adjacent to) appropriate apexes of the undulating helix, e.g., (104 in FIG. 3) or may be loops specifically installed for the purpose shown here. It should be clear that the tether wire (306) is so placed that when it is removed by sliding it axially along the stent (302) and out of the loops (308), that the stent (302) unfolds into a generally cylindrical shape within the body lumen or cavity.

FIG. 17B shows an end-view of a folded stent (302) or stent-graft having a guidewire (304) within the inner surface of the stent (302) and with the tether wire (306) within the loops (308). The end view of the folded stent (302) shows it to be folded into a form which is generally C-shaped. When expanded by removal of the tether wire (306), the stent (302) in FIG. 17B assumes the form shown in end view in FIG. 17C. There may be seen the guidewire (304) within the lumen of the stent (302) and the loops (308) which were formerly in a generally linear relationship having a tether wire passing through them.

Figure 18C:
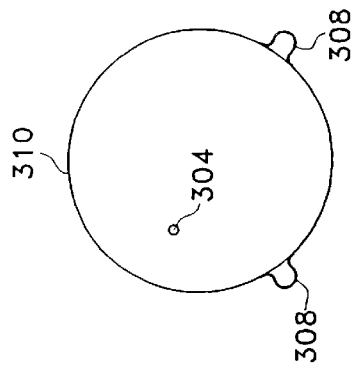
Figure 18B:
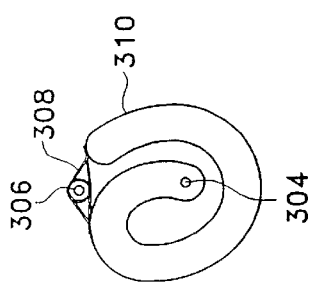
Figure 18A:
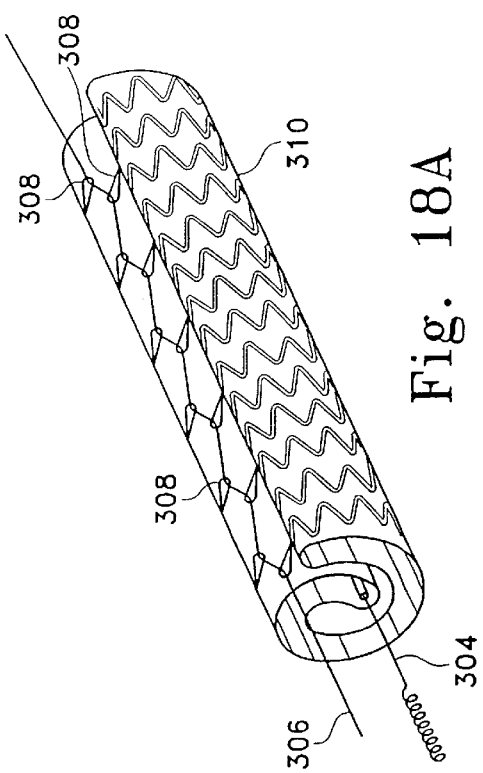

FIG. 18A shows a folded stent (310) (or stent-graft) in front quarter view which is similar in configuration to the stent (302) shown in FIG. 17A except that the stent (310) is rolled somewhat tighter than the previously discussed stent. The guidewire (304) is also inside the stent (310) rather than outside of it. Loops (308) from generally opposing sides of the stent (310) are folded into an approximate line so that the tether wire may pass through the aligned loops (308). FIG. 18B shows an end view of the stent (310), and in particular, emphasizes the tighter fold of the stent (310). When expanded by removal of the tether wire (306), the stent (310) in FIG. 18B assumes the form shown in FIG. 18C. In FIG. 18C may be seen the guidewire (304) within the lumen of the stent (310) and the loops (308) which were formerly in a generally linear relationship having a tether wire passing through them.

FIGS. 19A–C show an additional schematic procedure for deploying the stent (312) (or stent-graft) using a percutaneous catheter assembly (314).

In FIG. 19A may be seen a percutaneous catheter assembly (314) which has been inserted to a selected site (316) within a body lumen. The stent (312) is folded about the guidewire (319) and guidewire tube (318) held axially in place prior to deployment by distal barrier (320) and proximal barrier (322). The distal barrier (320) and proximal barrier (322) typically are affixed to the guidewire tube (318). The tether wire (306) is shown extending through loops (308) proximally through the catheter assembly's (314) outer jacket (324) through to outside the body.

FIG. 19B shows the removal of the tether wire (306) from a portion of the loops (308) to partially expand the stent (312) onto the selected site (316).

FIG. 19C shows the final removal of the tether wire (306) from the loops (308) and the retraction of the catheter assembly (314) from the interior of the stent (312). The stent (312) is shown as fully expanded.

Figure 20:
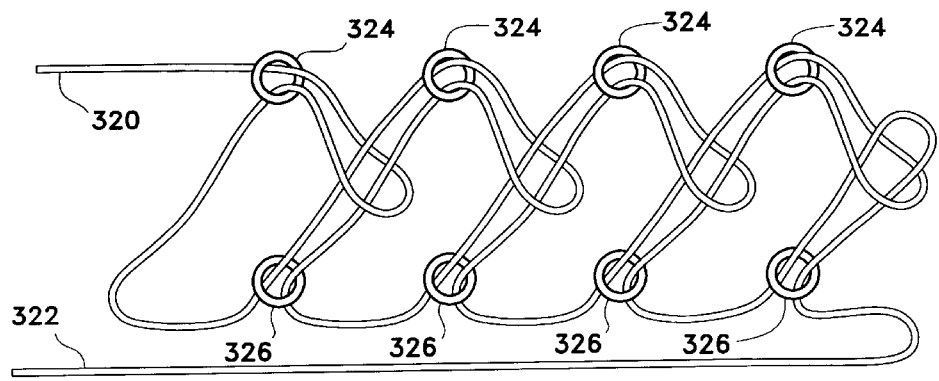
FIG. 20 shows a close-up view of a stent fold line using a preferred sack knot in the slip line.

FIG. 20 shows a close-up of a stent fold line having the familiar herringbone pattern of the "sack knot" used to close the fold in the stent. This knot is the one used to hold, e.g., burlap sacks of feed grain closed prior to use and yet allow ease of opening when the sack is to be opened. In this variation, the slip line has a fixed end (320) and a release end (322). Loops of the slip line pass through the eyelets (324) on the side of the stent fold associated with the fixed end (320) and are held in place by eyelets (326) on the side of the stent fold associated with the release end (322). The fixed end (320) is not typically tied to the stent so as to allow removal of the slip line after deployment. The eyelets (324 and 326) are desirable but optional. The eyelets (324 and 326) may be wire or polymeric thread or the like tied to the stent structure at the edge of the stent fold. If so desired, the loops may be dispensed with and the slip line woven directly into the stent structure. The self-expanding stent may be deployed by pulling axially on release end (322) as shown by the arrow in the drawing.

Figure 21:
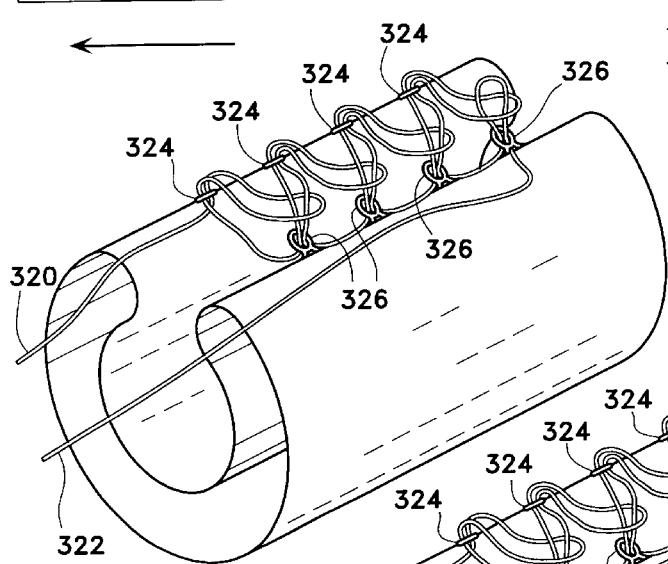
FIGS. 21 and 22 show front quarter views of folded stents or stent-grafts held in that folded position by a tether wire using a sack knot.
Figure 22:
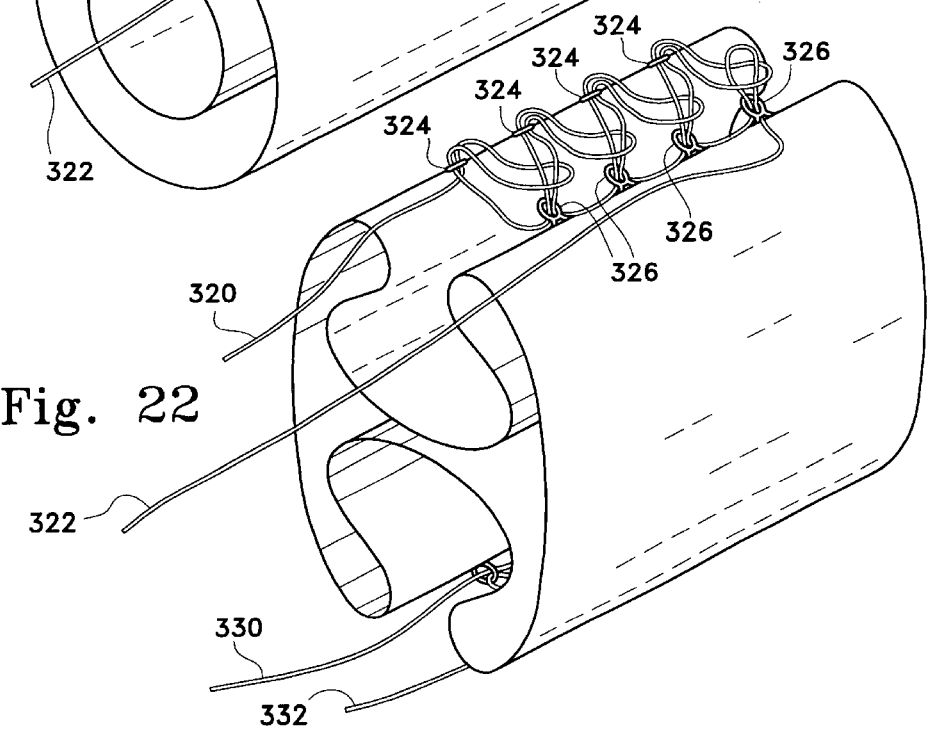

FIGS. 21 and 22 show front quarter views of folded stents using the knot shown in FIG. 20. FIG. 21 shows the use of a single stent fold similar in configuration to those described above. As was shown in FIG. 20, the fixed end (320) portion of the slip line is associated with a row of eyelets (324) which are tied or otherwise fixed to the stent. The release end (322) is associated with the other row of eyelets (326).

FIG. 22 merely depicts the use of multiple stent folds each having a fixed end (320 & 330) and a release end (322 & 332) on their respective slip lines.

The variations of the invention shown in FIGS. 20–22 may be introduced into the body using the procedures outlined above with relation to FIGS. 15–19.

Although we generally discuss the deployment of the stent or stent-graft using a catheter, often deployed percutaneously, it should be apparent that the procedure and the folded stent or stent-graft are not so limited. The folded stent or stent-graft may also be deployed through artificial or natural body openings with a sheath or endoscopic delivery device perhaps without a guidewire. Similarly, the stent or stent graft may be delivered manually during a surgical procedure.

Many alterations and modifications may be made by those of ordinary skill in the art without departing from the spirit and scope of the invention. The illustrated embodiments have been shown only for purposes of clarity and examples, and should not be taken as limiting the invention as defined by the following claims, which include all equivalents, whether now or later devised.

We claim as our invention:

1. A device comprising:
   a self-expanding stent having a longitudinal axis, said stent having a deployable configuration and an enlarged deployed configuration; and a removable slip line for holding said stent in the deployable configuration, wherein said removable slip line is woven into said stent along a longitudinal fold line of said stent using a sack knot so as to allow enlargement of said stent through movement of said slip line.

2. The device of claim 1 in which the self-expanding stent comprises loops along said fold line through which the slip line is introduced.

3. The device of claim 1 in which the stent comprises a super-elastic alloy.

4. The device of claim 1 in which the stent comprises a nickel-titanium alloy.

5. The device of claim 1 wherein the stent comprises at least one helically positioned member having undulating elements.

6. The device of claim 1 further comprising a graft attached to the stent.

7. The device of claim 6 in which the graft comprises a polymeric material.

8. The device of claim 6 wherein the graft additionally comprises reinforcing fibers.

9. The device of claim 6 wherein the graft additionally comprises radio-opaque markers.

10. The device of claim 7 in which the polymeric material comprises a fluoropolymer.

11. The device of claim 7 in which the polymeric material comprises a polyester terephthalate.

12. The device of claim 7 in which the polymeric material comprises a polyurethane.

13. The device of claim 10 in which the fluoropolymer comprises polytetrafluoroethylene.

14. The device of claim 13 in which the polytetrafluoroethylene is expanded.

* * * * *